United States Patent
Blessing et al.

(10) Patent No.: US 10,988,727 B2
(45) Date of Patent: Apr. 27, 2021

(54) FERMENTATION SYSTEMS

(71) Applicant: FRAUNHOFER-GESELLSCHAFT ZUR FOERDERUNG DER ANGEWANDTEN FORSCHUNG E.V., Munich (DE)

(72) Inventors: Daniel Blessing, Lausanne (CH); Tanja Holland, Alsdorf (DE); Markus Sack, Alsdorf (DE); Matthias Buntru, Aachen (DE); Simon Vogel, Aachen (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 370 days.

(21) Appl. No.: 15/304,618

(22) PCT Filed: Apr. 28, 2015

(86) PCT No.: PCT/EP2015/000867
§ 371 (c)(1),
(2) Date: Oct. 17, 2016

(87) PCT Pub. No.: WO2015/165583
PCT Pub. Date: Nov. 5, 2015

(65) Prior Publication Data
US 2017/0037421 A1 Feb. 9, 2017

(30) Foreign Application Priority Data
Apr. 28, 2014 (EP) .................... 14166157

(51) Int. Cl.
*C12M 1/34* (2006.01)
*C12N 5/04* (2006.01)
*C12N 15/82* (2006.01)
*C12N 5/00* (2006.01)
*C12N 5/071* (2010.01)
*C12N 5/14* (2006.01)
*C12N 5/16* (2006.01)
*A01H 4/00* (2006.01)

(52) U.S. Cl.
CPC ............. *C12M 41/36* (2013.01); *A01H 4/00* (2013.01); *C12N 5/0062* (2013.01); *C12N 5/04* (2013.01); *C12N 5/0602* (2013.01); *C12N 5/14* (2013.01); *C12N 5/16* (2013.01); *C12N 15/8257* (2013.01); *C12N 15/8258* (2013.01)

(58) Field of Classification Search
None
See application file for complete search history.

(56) References Cited

U.S. PATENT DOCUMENTS
3,958,364 A * 5/1976 Schenck ............... C02F 1/5236
435/101

FOREIGN PATENT DOCUMENTS
JP H02109973 A 4/1990
WO 2013/113504 A1 8/2013

OTHER PUBLICATIONS

Theegalaet al., A Computer Automated, Hydraulically Integrated Serial Turbidostat Algal Reactor (HISTAR): Mathmatical Modeling and Experimetnal Analysis. (1997). LSU Historical Dissertations and Theses. 6551 https://digitalcommons.lsu.edu/gradschool_disstheses/6551.*
Rusch and Christensen. "The Hydaulically Integrated Serial Turbidostat Algal Reactor (HISTAR) for Microalgal Production." Aquacultural Engineering, Apr. 2003, 27:249-264, Elsevier Science B.V.
Maeda et al. "Simultaneous Control of Turbidity and Dilution Rate Through Adjustment of Medium Composition in Semi-Continuous Chlamydomonas Cultures." Biotechnology and Bioengineering, Jul. 2006, 94(4)722-729, Wiley Periodicals, Inc.
Hellwig et al. "Plant Cell Cultures for the Production of Recombinant Proteins." Nature Biotechnology, Nov. 2004, 22(11)1415-1422, Nature Publishing, New York, NY.
PCT/EP2015/000867 International Search Report dated Aug. 18, 2015.

* cited by examiner

Primary Examiner — Allison M Fox
(74) Attorney, Agent, or Firm — Wagenknecht IP Law Group, PC

(57) ABSTRACT

The present disclosure pertains to novel cell cultivation and cell and/or cell-derived product production processes that have advantages over currently existing fermentation strategies. The processes and methods according to the present disclosure may be used for an efficient supply of highly viable and metabolically active eukaryotic cells for transient production platforms, as an alternative production process with advantages over currently applied processes (batch, fed-batch or perfusion strategies) and for generating metabolically highly active biomass for subsequent use for transient expression systems or infection by a virus or pseudovirus or in cell-free systems.

14 Claims, 14 Drawing Sheets

A)

B)

FERMENTATION SYSTEMS

CROSS REFERENCE TO RELATED APPLICATIONS

This is a national phase application of international patent application no. PCT/EP2015/000867, filed on Apr. 28, 2015, which itself claims priority to European application EP14166157, filed Apr. 28, 2014. All of the applications referred to in this paragraph are incorporated by reference in their entireties herein.

FIELD OF THE DISCLOSURE

The present disclosure pertains to novel cell cultivation and cell and/or cell-derived product production processes that have advantages over currently existing fermentation strategies. The processes and methods according to the present disclosure may be used for an efficient supply of highly viable and metabolically active eukaryotic cells for transient production platforms, as an alternative production process with advantages over currently applied processes (batch, fed-batch or perfusion strategies) and for generating metabolically highly active biomass for subsequent use for transient expression systems or infection by a virus or pseudovirus or in cell-free systems.

BACKGROUND

Manufacturing of biopharmaceuticals is subject to many changes, such as rising volume demands and more stringent safety requirements. In addition, product quality, product yields, production costs and facility utilization are important aspects for the biopharmaceutical industry. Thus there is continued interest in further optimizing and refining conventional manufacturing platforms and to develop novel ones that are capable of resolving current bottlenecks as well as to enable novel and innovative production processes.

The use of fermenters in the biotechnology industry as a rule currently involves batch, fed batch or continuous bioreactor processes for preparation of fermentation solutions, production of biomass and manufacture of fermentation products. The mode of feeding the bioreactors determines whether a bioreactor or fermenter is classified as batch, fed batch or continuous bioreactor.

If the bioreactor is only filled once without further feeding (i.e. addition of media containing nutrients) the bioreactor is operating in batch mode. The bioreactor will be allowed to run till completion. At the end of the run the fermentation is terminated and the products are harvested, before a new fermentation is initiated again.

These batch procedures customarily include inoculation of a nutrient medium with the desired culture, cultivation for a specific time under precisely defined conditions, and harvesting of the microorganisms and/or recovery of the desired products of metabolism.

In Detail Batch Fermentation:

A batch fermentation is once filled with medium and inoculated. After inoculation the reactor is a closed system except for a few additives like oxygen and base/acid for controlling the pH. This means that once the fermentation is started no additional media or nutrients will be fed into the reactor. So the reactor culture volume is constant over the entire process (except for volume losses due to evaporation). Several important cell culture parameters are changing over the process, e.g. cell density, viability, dissolved oxygen, nutrient and product concentration. The cell culture undergoes a lag, exponential and stationary growth phase. When harvest conditions are reached the process is finished and the total fermentation broth will be harvested. To produce more products, the process is repeated or scaled to larger vessels.

In Detail Repeated Batch Fermentation:

A repeated batch fermentation is operating in normal batch mode after inoculation. The culture parameters like cell density, dissolved oxygen, nutrient and product concentration are changing over the entire process. The bioreactor will be allowed to run till completion. At the end of the run the fermentation broth is harvested under sterile conditions but a fixed volume of fermentations broth remains in the bioreactor and served as the new inoculum. The reactor is filled with fresh medium again and a new batch fermentation cycle starts. Cells in that operation mode undergo a new adaption, exponential and stationary growth phase each cycle. The repeated batch fermentation increases the overall process efficacy of batch and fed-batch processes by saving the time for preparing the fermenter and inoculum. While ideally the repeated batch is essentially identical to the batch cultivation, memory effects and carry-over from the previous cultivation are of concern, especially for production of pharmaceutical proteins.

However, a number of disadvantages are associated with these several batch processes. In batch fermentations growth of microorganisms and living cells generally occurs under varying and sometimes unfavorable conditions. At the beginning of the fermentation the cells require time (lag-phase) to adapt to the medium. The viable cell density (inoculum viable cell count) is at its lowest level in the presence of the highest substrate concentration, which can even lead to substrate inhibition or to suppression of growth due to the high osmolarity of the medium.

In a continuous fermentation sterile nutrient solution is fed to bioreactor continually with a specific rate and an equivalent volume of fermentation broth is simultaneously removed from the bioreactor to keep the culture volume in the bioreactor essentially constant over the entire process.

The growth rates of the organism will be controlled by the rate the medium is pumped in depending on the maximal growth rate of the culture. The fresh medium rate (so called dilution rate) needs to be lower than 90% of the maximal specific growth rate of an organism. The relative low doubling times of mammalian and plant cells (approximately 1 per day) is resulting in low dilution rates and therefore the washed out fermentation broth have to be collected over longer time periods. This so called a hold step of the harvest has several disadvantages. First, the harvested cells are kept under unfavorable conditions, as the harvest container does not comprise the same level of complexity as the fermenter. Typically a number of parameters are not controlled anymore. The change in conditions leads to lower cell viability and cell rupture causes release intracellular contaminants such as host cell proteins and host cell DNA. Product quality can be compromised through several mechanisms including proteolytic degradation or altered post-translational modifications. The definition of a batch in regulatory terms is also more difficult. Batch-to-batch consistency is a critical issue because minor changes in the growth rate, which can e.g. be caused by subtle differences in media batches, can cause large changes in the process. For biopharmaceutical products such processes then have to be terminated and the products have to be rejected.

In Detail Continuous Fermentation (Chemostat/Turbidostat)

Both operation modes are continuous processes with a fixed reactor volume that aim for a constant cell density. In both processes fresh medium is continuously fed to the reactor while simultaneously the same volume of fermentation broth is harvested. The culture volume is kept constant over the entire process, thus the amount of fresh medium that is added has to be equal to the amount of culture broth that is removed. Fresh medium input and fermentation broth output therefore depend on each other.

In the chemostat process, fixed flow rates for adding the fresh medium (=feed rate) and removing the culture broth (=harvest rate) are used. The flow rates are identical and are called the dilution rate, i.e. the culture volume in the fermenter is maintained constant. Once the cell culture has adapted to the external conditions the process is in a stable steady state and the growth rate matches the feed rate. If the system is disturbed such that the growth rate is affected, which can for example be the case when a new batch of medium is used, or when metabolic products accumulate over time, the system can become unstable. In particular if the growth rate is reduced, the cells are washed out and the cell density decreases steadily. The increase of the cell number in the culture also depends on the volume. As a result, fermentation broth cannot be harvested at will without disturbing the process. Moreover, the cell density of a stable chemostat process is a result of the external conditions (nutrients, temperature, aeration . . . ) and cannot be defined otherwise by the operator. In the turbidostat process the dilution rate is controlled by the turbidity such that the cell density and culture volume in the fermenter remains constant over time. Culture broth is continuously removed from the fermenter and is stored in a collection vessel. Fermentations operated in the chemostat/turbidostat mode provide culture broth and products contained therein by continuously harvesting small fractions of the culture grown in the vessel. The small fractions have to be collected and stored over extended periods in a container. Especially for biopharmaceuticals such a hold-step is not desirable because it is a source of variation and can negatively impact the product quality. For example, cell-lysis may occur during the hold step, proteases may degrade the product or post-translational modifications may be affected which again increases the variation and has impacts on the product quality. Hold-steps are even more undesirable in cases where the cells or compositions derived from these cells comprise the product. The hold step reduces cell viability, metabolic activity and reproducibility.

Continuous fermentations are advantageous because they have a significantly higher space-time yield as compared to batch and fed-batch processes. Thus, they require a lower facility size for achieving the desired production capacity and this also means that investments for building the production facility are lower.

Despite the ideal characteristics of the continuous bioreactor, the process itself is sensitive and subjected to influence from various factors such as risks of contaminations, cell or biomass washouts, and changes in the biotic phase of the bioreactor.

Fed Batch is the intermediary model of bioreactor operation. A proper feed rate, with the right component constitution is required during the process. Fed-batch offers many advantages over batch and continuous cultures. From the concept of its implementation it can be easily concluded that under controllable conditions and with the required knowledge of the microorganism involved in the fermentation, the feed of the required components for growth and/or other substrates required for the production of the product can never be depleted and the nutritional environment can be maintained approximately constant or at the required level during the course of the fermentation. The production of by-products that are generally related to the presence of high concentrations of substrate can also be avoided by limiting its quantity to the amounts that are required solely for the production of the biochemical. When high concentrations of substrate are present, the cells get "overloaded", this is, the oxidative capacity of the cells is exceeded, and due to the Crabtree effect, products other than the one of interest are produced, reducing the efficacy of the carbon flux. Moreover, these by-products prove to even "contaminate" the product of interest, such as ethanol production in baker's yeast production, and to impair the cell growth reducing the fermentation time and its related productivity (Chmiel 2006).

In Detail Fed Batch Fermentation:

A fed-batch fermentation starts with a classical batch phase. When certain conditions are reached the feed is started, i.e. additional nutrients are provided. In this operation mode the reactor culture volume is constant in the batch phase and in the feeding phase the volume increases. In this mode also several culture parameters are changing and the cells undergo classical growth phases. Like in the batch fermentation the total reactor volume will be harvested at the end of the process.

In batch and fed-batch fermentation the cell viability is declining in the later stages and the harvest time point has to be selected carefully to ensure high and consistent product quality. Cells can experience high stress due to metabolic burden. Dying and rupturing cells release intracellular matter, e.g. host cell proteins and DNA as well as product related impurities into the media, which can also be of concern.

However, almost all therapeutic antibodies are currently produced using fed-batch fermentation strategies or perfusion-strategies. Certain regulatory aspects such as batch definition and time requirements for process development (technical runs, repeatability) and general concerns (see hold step, product stability and quality) as well as a typical reluctance within the pharmaceutical industry for new or different technologies have all contributed to the huge dominance of fed-batch methods. This is even though there are several issues that are problematic, as e.g. product quality and post-translational modifications, in particular for antibody products where N-glycosylation is a critical property. In many cases fed-batch cultures are incubated for long times to maximize yields, but cell viability significantly decreases towards the end of the cultivation period, liberating intracellular product, host cell proteins and host cell DNA. The down-side of this is or can be lower product quality or higher product heterogeneity (e.g. glycoforms), eventually leading to a higher failure rate (out-of specification batches) or lower product performance (i.e. clinical efficacy).

Furthermore, low running-to-set-up-times ratio for batch and fed-batch fermentations is currently compensated by investments of men-power and infrastructure. Switching to continuous modes can sometimes circumvent this but this is not always possible and not always desirable. Problems related to product homogeneity occurring during stationary phase in batch/fed-batch/repeated batch fermentation can be addressed or avoided by harvesting/terminating the process before the stationary phase is reached. However, significantly lower product yields then have to be accepted. Differences in product quality are a frequent cause for batch rejection, i.e. the whole material has to be thrown away and the invested costs are not recovered.

Recently production technologies using transient gene expression in eukaryotic cells have gained considerable interest (Derouazi, Girard et al. 2004 Biotechnol Bioeng;

Geisse, Jordan et al. 2005 Methods Mol Biol; Hacker, Derow et al. 2005 J Biotechnol). This is for several reasons, including higher yields as compared to transgenic systems (e.g. transgenic plants), short production cycles (days vs. month or even years), fast response times, particularly in emergency situations (pandemics, personalized medicines) and faster product and clinical development. Transient production systems require large amounts of wild type (i.e. non-transformed) cells for transfection/transformation because the cells are not incubated over long time periods and cell growth and cell division is typically low or does not occur at all. It is obvious that the wild type cells used as hosts for transient gene expression critically affect the yield and quality of the resulting products. Moreover, a high reproducibility is very important for products that are destined for clinical trials.

For transient production technologies the reproducible production of highly viable cell material is one of the most crucial bottlenecks.

Cell-free systems, including in-vitro transcription and in-vitro translation have also gained significant interest, in particular for High-Throughput screening and synthetic biology applications. Particular advantages are (amongst others) that cell-free systems can be modified in ways not amenable to whole cells, that nucleic acids can be directly added without the need for technologies to deliver them through cell walls and cell membranes into the cell, experiments can be standardized and that there are multiple ways for measuring readouts. Cell-free systems are particularly amenable to down-scaling and automation. As for transient expression systems, reproducible production technologies for highly active components required for cell-free systems currently represent a significant bottleneck.

Therefore, it was the object of the present disclosure to overcome the disadvantages of the current fermentation technologies for providing improved cell biomass or cell-derived products.

SUMMARY OF THE DISCLOSURE

The novel cell cultivation and cell and/or cell-derived product production processes provides several advantages over the currently existing fermentation strategies.

The main difference of the novel process to the continuous chemo-/turbidostat process is the variable culture volume and the independence of feed rate and harvest rate. In contrast to chemo-/turbidostat the culture volume in the processes according to the present disclosure is neither constant over the entire process like in a batch or chemo-/turbidostat process nor just simply rising over the entire process like in a fed batch process. The variable culture volume and the uncoupled feed rate and harvest rate are major characteristics of the novel process. The different processes can be distinguished by comparing the culture volume, cell density, feed rate and harvest rate (see FIGS. 9, 10 and 11).

The feed stream in the process of the present disclosure is controlled by the cell density and therefore indeed continuous since the cells are constantly growing at their maximal growth rate but it is not fixed or predefined like in a chemostat or fed batch fermentation (FIG. 11).

In contrast to batch and fed-batch fermentations, where the entire culture is harvested at the end of the process, and to chemo-/turbidostat processes, where incremental amounts of the culture are harvested continuously, the process according to this invention allows harvesting of any volume within the working range at any time. The working range is given by the actual culture volume minus the minimal volume that is retained.

Therefore, the present disclosure pertains to novel cell cultivation and cell and/or cell-derived product production processes that have advantages over currently existing fermentation strategies. The processes and methods according to the present disclosure may be used for an efficient supply of highly viable and metabolically active eukaryotic cells for transient production platforms, as an alternative production process with advantages over currently applied processes (batch, fed-batch or perfusion strategies) and for generating metabolically highly active biomass for subsequent use for transient expression systems or infection by viruses or pseudoviruse or in cell-free systems. The present disclosure pertains to a continuous/semi-continuous cell cultivation strategy that allows harvesting of reproducible fermentation broth at variable time points and variable volumes, which for example provides particular advantages for continuous downstream processing strategies.

The present disclosure may also be used to increase space-time yields of the production of biopharmaceuticals derived from stable transgenic cell lines. Furthermore, the processes and methods according to the present disclosure may be used to implement more efficient up- and downstream processes to increase production facility utilization.

Furthermore, cell cultivation process according to the present disclosure enables the arbitrary and repeated harvesting of any volume at any time without disturbing the growth of the cells, wherein 0<harvested volume <(actual volume−minimal volume). One of the advantages of the processes according to the present disclosure is that the continuous cell cultivation process does not require a vessel for collecting fermentation broth over extended periods of time and/or the feed is regulated and the harvest can be executed arbitrarily, such that the growth of the cells is maintained and not significantly disturbed by the harvesting procedure.

In a first aspect, the present disclosure pertains to cell-density regulated cell cultivation processes for the production of eukaryotic cells and/or an eukaryotic cell-derived product, wherein the cell density during the cell cultivation is regulated by adjusting the volume of the cell culture comprising the cells and a nutrient medium in a cultivation vessel, said process comprises the following steps:
a) growing the cells in a cell culture having a variable cell culture volume, wherein the culture volume is not regulated to be constant over the entire cell cultivation process,
b) measuring the cell density in the cell culture with a density sensor,
c) regulating the cell density in the cell culture by adding an appropriate volume of the nutrient medium to the cell culture to keep the cells in the growth phase,
d) harvesting a fraction of the cell culture at a desired cell density, wherein the harvested fraction comprises cells and/or a cell-derived product, and wherein the cell culture volume in the vessel is not kept constant continuously by adding nutrient medium into the vessel after harvesting said fraction and/or wherein the volume of the harvested fraction is not immediately replenished by adding nutrient medium into the vessel,
e) repeating one or all of the aforementioned steps in the order set forth to allow a repeated harvest of cell culture fractions, and
f) optionally processing the harvested cells and/or cell-derived products.

In one aspect, the present disclosure relates to cell-density regulated cell cultivation processes for the production of eukaryotic cells and/or a eukaryotic cell-derived product, wherein the cell density during the cell cultivation is regulated by adjusting the volume of the cell culture comprising the cells and a nutrient medium in a cultivation vessel, said process comprises the following steps:

a) growing the cells in a cell culture having a variable cell culture volume, wherein the culture volume is not regulated to be constant over the entire cell cultivation process,
b) measuring the cell density in the cell culture with a density sensor,
c) regulating the cell density in the cell culture by adding an appropriate volume of the nutrient medium to the cell culture to keep the cells in the growth phase,
d) harvesting a fraction of the cell culture at a desired cell density, wherein the harvested fraction comprises cells and/or a cell-derived product, and wherein the volume of the harvested fraction is not immediately replenished by adding nutrient medium into the vessel,
e) repeating one or all of the aforementioned steps in the order set forth to allow a repeated harvest of cell culture fractions, and
f) optionally processing the harvested cells and/or cell-derived products.

In another aspect, the present disclosure relates to cell-density regulated cell cultivation processes for the production of eukaryotic cells and/or a eukaryotic cell-derived product, wherein the cell density during the cell cultivation is regulated by adjusting the volume of the cell culture comprising the cells and a nutrient medium in a cultivation vessel, said process comprises the following steps:

a) growing the cells in a cell culture having a variable cell culture volume , wherein the culture volume is not regulated to be constant over the entire cell cultivation process,
b) measuring the cell density in the cell culture with a density sensor,
c) regulating the cell density in the cell culture by adding an appropriate volume of the nutrient medium to the cell culture to keep the cells in the growth phase,
d) harvesting a fraction of the cell culture at a desired cell density, wherein the harvested fraction comprises cells and/or a cell-derived product, and wherein the cell culture volume in the vessel is not kept constant continuously by adding nutrient medium into the vessel after harvesting said fraction
e) repeating one or all of the aforementioned steps in the order set forth to allow a repeated harvest of cell culture fractions, and
f) optionally processing the harvested cells and/or cell-derived products.

Another aspect of the present disclosure relates to methods for the preparation of cell free extract for an in vitro translation comprising the steps of:
i) Cultivating and harvesting cells according to a process of the present disclosure,
ii) Obtaining of a cell-free extract of the cultured cells by subjecting the harvested cells to an extraction treatment using.

In a further aspect, embodiments of this disclosure relate to method for generating a stable cell line comprising the steps of:
i) Cultivating and harvesting cells according to a process of the present disclosure,
ii) Transforming the harvested cells with a nucleic acid to obtain a stable cell line.

In still another aspect, embodiments of this disclosure provide methods for the generation of plant cell material in the form of a medium-deprived, porous structured and non-tissue multilayer cell pack and for the subsequent maintenance of said cell pack, comprising the steps of
(i) providing a cell pack having a porous structure by separating cells from a plant cell suspension culture, wherein the cells were cultivated by a method according to the present disclosure, and wherein the content of the liquid comprised by the cell pack is reduced and adjusted to correspond to a cell pack density between 0.1 and 0.9 g wet cell weight per $cm^3$, thereby establishing the medium-deprived and porous structured nature of said cell pack, and
(ii) incubating said medium-deprived and porous structured cell pack in a non-liquid environment under a relative humidity of 50 to 100%.

Before the disclosure is described in detail, it is to be understood that the terminology used herein is for purposes of describing particular embodiments only, and is not intended to be limiting. It must be noted that, as used in the specification and the appended claims, the singular forms "a," "an" and "the" include singular and/or plural reference unless the context clearly dictates otherwise. It is moreover to be understood that, in case parameter ranges are given which are delimited by numeric values, the ranges are deemed to include these limitation values.

DETAILED DESCRIPTION OF THIS DISCLOSURE

Figure 1:
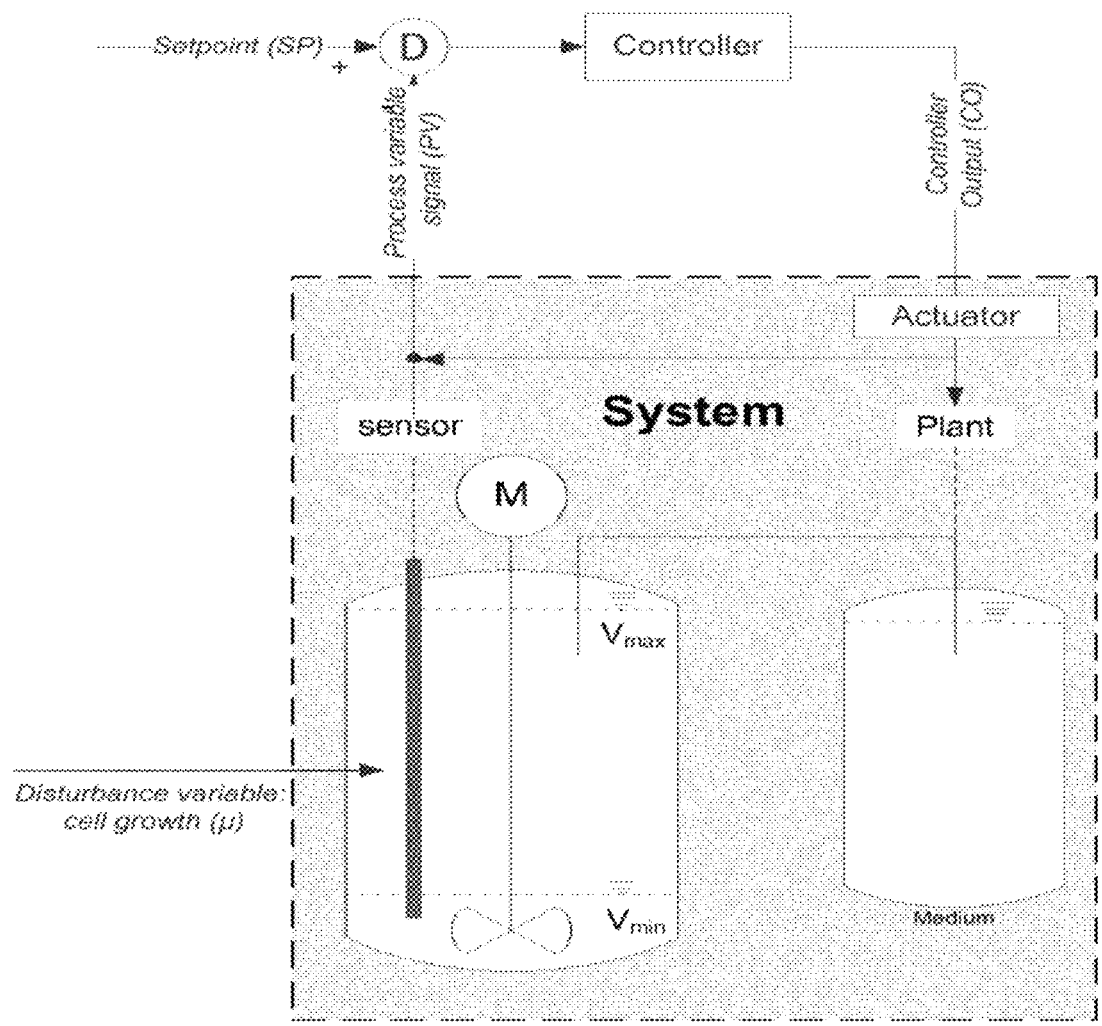
FIG. 1 is a scheme of a cultivation system according to the present disclosure.

The present disclosure relates to novel processes and methods for producing eukaryotic cells (biomass) and/or eukaryotic cell-derived products like proteins in a highly consistent and reproducible manner. The processes of the present disclosure are cell-density regulated cell cultivation processes, wherein adjusting the volume of the cell culture in the cultivation vessel regulates the cell density in the cell culture. The processes and methods are suited for both plant and mammalian-based systems, in a highly consistent and reproducible manner, wherein the processes are robust and reproducible production better meets regulatory requirements. One advantage of the processes of the present disclosure is the ability for producing improved cells for screening and product development due to a better comparability, batch-to-batch consistency and lower variation. Furthermore, the ability to provide highly viable (exponentially growing) cells with the disclosed processes, gives the advantages of (i) high transformation efficiencies, (ii) productivities (product yields, enzymatic activities) and (iii) high metabolic activity (application in cell-free systems). The processes and methods of the present disclosure are more economical due to an increased running-to-setup-time ratio, the requirement of less manpower and increased space-time-yields. In particular, the harvest time and the harvested volume is more flexible with the disclosed processes, allowing to react to less predictable demands when running several small production campaigns (personalized medicines or product development). The methods provide many of the advantages of continuous fermentation strategies (chemostat, perfusion) but circumvent/solve problems related to cell viability, product stability and quality during the hold-step.

The processes and methods according to the present disclosure consist of a novel way for controlling cell density (or any other property that relates to cell density, biomass density, cell concentration or cell number per volume) during a fermentation process. This is achieved by adjusting the biomass by changing the volume of the fermentation broth (i.e. cell culture). A control loop may be used where a sensor continuously measures the biomass (input signal) and a controller generates an output signal that triggers for example a pump to add an appropriate volume from a medium reservoir to the cultivation vessel, thereby changing the cell culture volume. By adding the appropriate volume the cell density is maintained constant over time (alternatively, a time-dependent function for the cell density can be defined and accordingly controlled). By doing this, the cells are constantly kept in the growth phase. The fermenter is operated between a minimal and maximal fill level. The volume that is withdrawn can be variable within this minimal and maximal range. The minimal and maximal volume is given by the vessel geometry. The minimal volume is that volume that has to be retained in the fermenter to ensure that all installations like the probes/sensors or the stirrer are in a sufficient contact to the fermentation broth to provide a proper measurement, mixing and control of the process. The maximal filling level is defined by the volume, which ensures that no flooding of the vessel with fermentations broth or foam can happen. If the maximal fill level is reached, fermentation broth has to be withdrawn. Alternatively, the control loop can be changed, i.e. to obtain higher cell densities. The fermentation broth that can be harvested at different times and variable volumes is highly consistent and reproducible. Those skilled in the art will also appreciate that an automated harvesting function can be implemented, for example to prevent the actual cell culture volume to increase over the maximum volume, or to enable remote harvesting. The automated harvest function can e.g. be realized by using a level sensor in combination with externally controlled pump by an e.g. analog or digital output signal.

It was an object to provide a new and efficient eukaryotic cell production technology, i.e. for using the produced cells in transient production technologies. Recently transient production technologies using eukaryotic cells have gained considerable interest. This is for several reasons, including (i) higher yields as compared to transgenic systems (e.g. transgenic plants), (ii) short production cycles (days vs. month or even years), fast response times, particularly in emergency situations (pandemics, personalized medicines) and faster product and clinical development.

Therefore, in advantageous embodiments, the processes and methods according to the present disclosure are used to provide cells (biomass) that are subsequently used as host cells for transient production. This means that these cells will subsequently be transfected/transformed by appropriate means and incubated to produce molecules of interests (products). The cell viability is of critical importance for transient production platforms utilizing cell suspensions (both animal and plant cells). For the transient production there is also a need of large amounts of homogeneous and reproducible starting material (cells).

One advantage of using a process according to the present disclosure is that in some embodiments no stationary phase occurs and the cell viability is maintained throughout the whole productions process and therefore the process has advantages compared to batch, fed-batch und perfusion methods.

A further advantage is that the processes and methods of the present disclosure can be used for running a "fermentation cascade" by using a first cultivation step according to the disclosed methods for producing the cell biomass (under conditions that repress expression of the recombinant gene), then transferring these cells into another fermenter and then running a second phase where gene-expression is induced or cells are infected with viruses or cells are incubated under conditions different from the first cultivation step. This is particularly advantageous for fermentation cascades where the second phase is shorter than the cell production phase (better space-time-yields) or where a physical separation is required, e.g. when cells are infected by a virus or a pseudovirus.

For the production of cell free extracts (lysates) for in vitro translation there's a need of large amounts of homogenous starting material. To ensure an optimal productivity of the resultant lysates the cells have to be in an exponential growth phase characterized by high metabolic activity and high viability. In addition the cell density at the point of harvest plays a critical role.

Conventionally cell cultures are grown in batch mode to a desired cell density, harvested and immediately processed. This requires a high flexibility in terms of time, as growth rates vary in large fermentation processes making a specific harvest point not precisely predictable. Furthermore an optimal adaption of cells to the culturing process cannot be guaranteed in batch mode. Processing of the cell material to a highly active lysate is another important factor. The established protocols for the production of plant based cell free lysates are often time-consuming and cost-intensive.

Therefore, the processes and methods of the present disclosure are ideally suited to produce eukaryotic cells that are subsequently used to prepare such "cell-free systems" for gene expression and/or protein production. This is simply because these systems do also require consistent and reproducible and highly viable cells as starting material. Due to the possibility of the continuous controlled fermentation of cell cultures in an exponential growth phase and at a constant cell density, cell material which leads to lysates with optimal productivity can be harvested at any time and required volume within the min/max range of the vessel. The continuous fermentation for several months also ensures an optimal adaption for the cells to the fermentation conditions. The resultant consistent cell starting material greatly influences the quality of the processed final product. During processing of the cell material to a lysate the costs for protoplastation could be reduce more than hundredfold by replacing conventional enzymes by liquid cellulases and pectinases originally designed for food industry. At the same an improved protoplastation per time unit has been observed. The usage of these enzyme preparations permits the commercial production of the plant-based lysate at usual market prices. Further modifications to the protocol described by Komoda et al. (2004) like altered buffers, wash and centrifugation steps, and the use of a discontinuous instead of a continuous Percoll gradient led to a faster production as well as an easier scalability.

There are several further advantages that can be addressed by the processes and methods of the present disclosure like providing a highly consistent and reproducible cell biomass for subsequent use for transfection/transformation to produce molecules of interest by transient expression, providing a continuous cell cultivation strategy that allows harvesting of reproducible fermentation broth at variable time points and variable volumes. Further, the processes and methods of the present disclosure continuously provide exponentially growing cells with a high viability.

Furthermore, the processes and methods of the present disclosure solve the following problems. In continuous fermentations in the prior art a cell-derived product and/or the cell containing cell culture has to be harvested over an extended period of time, and the harvested material therefore is further incubated (as so called Hold-step). This Hold-step is problematic because (i) cell viability will decrease and/or (ii) product quality can be compromised. Consequently the definition of a batch is more difficult. Furthermore, continuous fermentations of plant suspension cells is technically challenging because the continuous removal of the suspension at low flow rates leads to clogging of the harvest pipes, essentially terminating the fermentation process. Further, batch and fed-batch fermentations suffer from a low (uneconomical) running-to-set-up-times ratio. Furthermore, product homogeneity (e.g. N-glycosylation of antibodies) is a critical issue for batch and fed-batch fermentation of mammalian-cells, because cell viability decrease towards the end of the fermentation, typically resulting in cell lysis, release of intracellular product (different N-glycosylation), host cell proteins and host cell DNA. The processes and methods of the present disclosure solve these problems.

Surprisingly, the inventors of the processes and methods according to the present disclosure show:

Continuous generation of a highly consistent and reproducible cell biomass

Robustness of the semi-continuous cultivation strategy (process times of more than 64 days achieved)

Increased space-time-yields (plant cell biomass) compared to repeated batch cultivation Dissolved oxygen regulation ensures constant exponential growth rates Successful cultivation of different plant suspension cells (*Nicotiana*, *Pyrus* and *Sorbus* species) during several processes Successful application of generated plant cells for transient gene expression and production of different antibodies Application of BY-2 plant cells for cell-free systems demonstrated Increase/decrease of cell concentration within a process Implementation of an automated harvest procedure (reducing "hands-on-time")

In summary, the present disclosure pertains processes and methods having the ability to produce cells (biomass) in a highly consistent and reproducible manner as a critical requirement for using transient production platforms for producing molecules for therapeutic applications.

Another direct effect is that the processes and methods of the present disclosure are ideally suited to provide highly viable (exponentially grown) cells, giving the advantages of (i) high transformation efficiencies and (ii) productivities (product yields, enzymatic activities, etc.). Apoptotic or dead cells that can give rise to impurities; proteases and other undesirable effects are concurrently reduced.

Yet another effect of the processes and methods of the present disclosure are the delivering of highly viable, consistent and reproducible cells that can be used to prepare/derive components for cell-free systems.

Another effect is that the running-to-setup-time ratio is increased and the advantage is that production gets cheaper and faster and requires less manpower. This is also a main advantage for microbial systems where inducible expression is used and a clear separation of a growth and a production phase can be made.

Yet another effect is that the harvest time and the harvested volume is more flexible. This is an advantage when reacting to the less predictable demands of running several small production campaigns, as for example can be expected when producing personalized medicines or in a product development cycles when directly responding to the results of the previous cycle.

Yet another effect is that the processes and methods of the present disclosure do not need a hold-step, i.e. it provides many of the advantages of continuous fermentation strategies (chemostat) but circumvents problems related to cell viability, product stability and quality during the hold-step.

This feature eliminates a significant bottleneck in downstream processing as it allows for better equipment utilization by reduction of idle time.

Advantageous embodiments of the present disclosure pertains to cell-density regulated cell cultivation processes for the production of eukaryotic cells and/or a eukaryotic cell-derived product, wherein the cell density during the cell cultivation is regulated by adjusting the volume of the cell culture comprising the cells and a nutrient medium in a cultivation vessel, said process comprises the following steps:
a) growing the cells in a defined volume of the cell culture,
b) measuring the cell density in the cell culture with a density sensor,
c) regulating the cell density in the cell culture by adding an appropriate volume of the nutrient medium to the cell culture to keep the cells in the growth phase,
d) harvesting a fraction of the cell culture at a desired cell density, wherein the harvested fraction comprises cells and/or a cell-derived product,
e) repeating one or all of the aforementioned steps in the order set forth to allow a repeated harvest of cell culture fractions, and
f) optionally processing the harvested cells and/or cell-derived products.

The term "defined volume" refers to a defined starting volume of the cell culture wherein the cells are growing. After the initial growing phase, the cells are growing within a defined volume range in the fermentation vessel, and wherein adjusting the volume of the cell culture regulates the cell density. The defined volume as a starting volume could also be mentioned as a minimal volume of the cell culture.

Further advantageous embodiments of the present disclosure pertains to cell-density regulated cell cultivation process for the production of eukaryotic cells and/or an eukaryotic cell-derived product, wherein the cell density during the cell cultivation is regulated by adjusting the volume of the cell culture comprising the cells and a nutrient medium in a cultivation vessel, said process comprises the following steps:
a) growing the cells in a cell culture having a variable cell culture volume, wherein the culture volume is not regulated to be constant over the entire cell cultivation process,
b) measuring the cell density in the cell culture with a density sensor,
c) regulating the cell density in the cell culture by adding an appropriate volume of the nutrient medium to the cell culture to keep the cells in the growth phase,
d) harvesting a fraction of the cell culture at a desired cell density, wherein the harvested fraction comprises cells and/or a cell-derived product, and wherein the cell culture volume in the vessel is not kept constant continuously by adding nutrient medium into the vessel after harvesting said fraction and/or wherein the volume of the harvested fraction is not immediately replenished by adding nutrient medium into the vessel;
e) repeating one or all of the aforementioned steps in the order set forth to allow a repeated harvest of cell culture fractions, and
f) optionally processing the harvested cells and/or cell-derived products.

The term "cell density" or "cell mass density" refers to the number of cells per unit volume in a cell culture (number of cells per volume of culture medium, mass of cells per volume (g/L), packed cell volume (%), wet or dry cell weight per volume (g/L), cell volume per volume of culture volume). Cell density includes also any other property that relates to cell density, biomass density, cell volume and concentration or cell number per volume.

The term "cell culture" refers to the cultivation of cells from a multicellular organism like an animal or a plant. According to the present disclosure a cell culture comprises eukaryotic cells and a liquid nutrient medium (cell growth medium or culture medium).

The term "cell-derived product" as used herein refers to any product synthesized by the cell or a product made in the cultivation vessel using a product synthesized by the cell. Cell-derived product also comprises a product generated in the cultivation vessel with the help of a cell component, e.g. a product converted from a substrate added to the cell culture by enzymes produced/derived from the cells. Cell-derived products include (but is not limited to) proteins like recombinant proteins, in particular proteins, which are secreted into the cell culture medium. Cell-derived products also include viruses. Cell-derived products also comprise components derived from the cells, such as membranes, cell walls, organelles, proteins, enzymes, nucleic acids, ribosomes, pigments, primary and secondary metabolites. Moreover, cell-derived products also comprise cell extracts or fractions (mixtures containing any combination of the before mentioned components).

According to a preferred embodiment, the eukaryotic cells comprised in the cell culture are native (e.g. wild-type) or non-transgenic cells that, before performing the second cultivation step, are transformed with at least one expression vector comprising at least one heterologous nucleic acid sequence preferably being operably linked to a functional promoter, wherein said at least one heterologous nucleic acid sequence codes for a desired cell-derived product to be accumulated and harvested.

The cultivated and produced eukaryotic cells includes human, animal and plant cells, in particular plant suspension cells, insect cells or mammalian cells. Examples for plant cells are cells from *Nicotiana tabacum* (e.g. BY-2, NT1, etc), *Dautus carota, Taxus* sp., *Catharanthus roseus, Physcomitrella patens, Zea mays, Glycine max, Nicotiana benthamiana, Arabidopsis thaliana, Pyrus communis, Sorbus torminalis*. Examples for insect cells are cells from Sf9, Sf21 or *Trichoplusia ni* (High Five). Examples for mammalian cells are HEK, CHO, BHK, EB66, MDCK (Madin Darby canine kidney) cells, or human cells like PER.C6, Hep G2, etc.

In some advantageous embodiments, the cell culture is added into the cultivation vessel as a starter culture, prepared for example in advance and outside the cultivation/fermentation vessel.

A "starter culture" as used herein is a microbiological culture, which actually performs fermentation. These starters usually consist of a cultivation medium that has been well colonized by eukaryotic cells used for the fermentation/cultivation.

In an embodiment of the present disclosure, a semi-continuous cultivation process is operated as follow:
Inoculation of 1.5 L Medium (minimal Volume) within a 7 L Bioreactor
Cultivation with over-pressure of 0.1 bar, pH not controlled, constant air supply of 500 mL/min, controlled temperature of 26° C. and 30% dissolved oxygen (controlled by regulating the stirrer speed 100-300 rpm)
Initial batch-Phase depending on the cultivated cells (BY-2 cells 4 days)
Start of the control loop to regulate biomass concentration (e.g. 100 g/L BY-2 cells)

Continuous growth of the cells coupled to an increasing reactor volume, due to a feed of fresh and sterile medium (supply of medium by refilling the reservoir with sterile medium)

Harvest necessary when maximal filling volume is reached, automated

Within the range of minimal to maximal volume time independent harvest of varying suspension volumes possible.

As mentioned above, the processes of the present disclosure consist of a novel way for controlling cell density during a fermentation/cultivation process. This is achieved by adjusting the biomass by changing the volume of the fermentation broth. In some advantageous embodiments a control loop is used where a density sensor continuously measures the biomass (input signal) and a controller generates an output signal that triggers for example a pump to add an appropriate volume from a medium reservoir to the fermentation vessel. By adding the appropriate volume the cell density is maintained constant over time (alternatively, a time-dependent function for the cell density can be defined and accordingly controlled). By doing this, the cells are constantly kept in the growth phase. The fermenter is operated between a minimal and maximal fill level. The volume that is withdrawn can be variable within a certain range. The range is defined by the minimal volume that has to be retained in the fermenter and the maximal filling volume of the vessel. If the maximal fill level is reached, fermentation broth has to be withdrawn. Alternatively, the control loop can be changed, i.e. to obtain higher cell densities. The fermentation broth that can be harvested at different times is highly consistent and reproducible.

In a first step in an advantageous embodiment, the cells were grown in a cell culture having a variable cell culture volume, wherein the culture volume is not regulated to be constant over the entire cell cultivation process. In particular, the volume of the cell culture is changing significantly over the process time. This is due to the arbitrary harvesting that is performed by the operator, while the addition of culture media is regulated by the cell density. During periods where no harvesting occurs, the volume of the cell culture increases. At times of harvest, the volume of the cell culture decreases arbitrarily (i.e. as chosen by the operator) but within the defined volume range. The volume range is defined as being equal to or lower than the actual culture volume minus the minimal culture volume.

This is in particular in contrast with processes in which the cell culture volume is kept "constant continuously" or in particular "essentially constant continuously", e.g. as done for chemostat and turbidostat processes or with processes in which the harvested cell culture is "replenished immediately".

Within the context of this invention "constant", in particular "essentially constant" means that short term fluctuations are observed and that the average value over an extended time window is maintained at the desired value within experimental limitations. To be more precise, short term means time periods of less than 10 minutes and extended time window refers to a time period of more than 30 minutes. Furthermore, "constant continuously", in particular "essentially constant continuously" refers to a time period of at least 12 h, preferably of 24 h, more preferably of 48 h and most preferably of at least 72 h.

In a second step, the cell density in the cell culture is measured with a density sensor. In advantageous embodiments, the cell density is measured by a density sensor, whereby the density sensor is selected from the group consisting of sensor based on turbidity measurements, laser scatter measurements, NIR measurements or other spectroscopic measurements, or capacitive measurements or at line systems like cell counter or any other methods which measure cell density and allow for feedback-control. In some embodiments, a density sensor measures the cell density in the cell culture continuously.

In a third step, the cell density in the cell culture I regulated by adding an appropriate volume of the nutrient medium to the cell culture to keep the cells in the growth phase. He "growth phase" be defined as the first phase within interphase, from the end of the previous M phase until the beginning of DNA synthesis, is called G1 (G indicating gap). During this phase the biosynthetic activities of the cell, which are considerably slowed down during M phase, resume at a high rate. The duration of G1 is highly variable, even among different cells of the same species. In this phase, cell increases its supply of proteins, increases the number of organelles (such as mitochondria, ribosomes), and grows in size.

In further embodiments, the appropriate volume of the nutrient medium is transferred into the cell culture in the cultivation vessel from at least one nutrient medium reservoir.

In some advantageous embodiments, the cell density is regulated by using a control loop comprising a density sensor continuously measuring the cell density (input signal) and a controller generating an output signal that triggers a pump or valve for adding the appropriate volume of the nutrient medium to the cell culture.

In some embodiments, the appropriate volume is added from a medium reservoir to the fermentation vessel by using a pump, or it is driven by gravity or pressure and controlled via a valve.

In further embodiments, the cell density in the cell culture is regulated to be constant over time or to be a specific time-dependent function for the cell density. Furthermore, the cultivation vessel can be operated between a minimal and a maximal cell culture filling level.

In a forth step, a fraction of the cell culture can be harvested at a desired cell density, wherein the harvested fraction comprises cells and/or a cell-derived product, and wherein the cell culture volume in the vessel is not kept constant continuously, in particular not kept essentially constant by adding nutrient medium into the vessel after harvesting said fraction.

A mentioned above, the volume of the cell culture is changing significantly over the process time. This is due to the arbitrary harvesting that is performed by the operator, while the addition of culture media is regulated by the cell density. During periods where no harvesting occurs, the volume of the cell culture increases. At times of harvest, the volume of the cell culture decreases arbitrarily (i.e. as chosen by the operator) but within the defined volume range. The volume range is defined as being equal to or lower than the actual culture volume minus the minimal culture volume. This is in particular in contrast with processes in which the cell culture volume is kept "essentially constant continuously", e.g. as done for chemostat and turbidostat processes or with processes in which the harvested cell culture is "replenished immediately". Within the context of this invention "essentially constant" means that short term fluctuations are observed and that the average value over an extended time window is maintained at the desired value within experimental limitations. To be more precise, short term means time periods of less than 10 minutes and extended time window refers to a time period of more than 30 minutes. Furthermore, "essentially constant continuously" refers to a time period of at least 12 h, preferably of 24 h, more preferably of 48 h and most preferably of at least 72 h.

In a forth step, a fraction of the cell culture can be harvested at a desired cell density, wherein the harvested fraction comprises cells and/or a cell-derived product, and wherein the cell culture volume in the vessel is not kept constant continuously, in particular not kept essentially constant by adding nutrient medium into the vessel after harvesting said fraction and/or wherein the volume of the harvested fraction is not immediately replenished by adding nutrient medium into the vessel;

The term "replenished immediately" refers to the replacement of the harvested cell culture by adding a similar amount of fresh media to the vessel. Within the context of the present disclosure, a similar amount of fresh media is defined as being the same volume as that of the harvested cell culture plus or minus 25%. Furthermore, "immediately" refers to a time period that is less than 12 h, preferably less than 6 h, and more preferably less than 3 h. "Immediately" could be also replaced by "directly" or "consecutively".

The fraction of the cell culture that can be harvested is within certain limits. After harvesting, the remaining volume has to be sufficient to support the process, i.e. a certain minimal volume of the cell culture has always to remain in the cultivation vessel. This minimal volume depends on a number of things including the vessel, biomass sensor, stirrer etc. However, at any given time any volume fraction of the current volume of the fermentation culture minus the minimum volume that has to remain in the cultivation vessel may be harvested As mentioned above, the processes and methods according to the present disclosure may be used for flexibly providing highly reproducible fermentation broth without the need of a hold step for subsequent downstream processing. The flexibility in terms of the harvest time point enables a higher utilization of the downstream infrastructure (unit operations) and staff. These particular features can be used to compensate delays occurring in downstream processing. For batch and fed-batch processes for production of biopharmaceuticals, idle time in downstream processing has to be accepted to ensure readiness at the harvest time as non-readiness would result in deviations from the specifications and thus lead to batch rejection with concurrent huge economical losses. In contrast, the processes and methods according to the present disclosure enable a postponing of the harvest time point by removal of appropriate volume fractions from the cultivation vessel. The resulting economical losses are much smaller as only a fraction of the overall production process is wasted.

In some embodiments, pluralities of cultivation vessels are connected to increase the cultivation volume. This would also enable to run the process longer since vessels can be taken out of the set to clean them (wall growth, filters, etc.) and reconfigure them (replace broken parts, recalibrate sensors) without having to stop the cultivation. The culture needs to be exchanged (e.g. "pumped") and mixed between the connected vessels to ensure that all vessels contain the same culture. In an advantageous embodiment, (i) at least one additional cultivation vessel is connected to the first cultivation vessel to increase the cultivation volume, (ii) the cell density in each connected cultivation vessel is the same and (iii) the cell culture is exchanged between the cultivation vessels. In another embodiment, a cultivation vessel could be removed from a set of two or more connected cultivation vessels to decrease the cultivation volume.

In further embodiments, the eukaryotic cells are cultivated in the presence of micro-carriers. A micro-carrier is a support matrix allowing for the growth of adherent cells in bioreactors like cultivation vessels. Several types of micro-carriers are available commercially including dextran-based (CYTODEX®, GE Healthcare), collagen-based (CULTISPHER®, Percell), macroporous gelatin-coated micro-carrier beads (CYTODEX®, Percell Biolytica AB), and polystyrene-based (SoloHill Engineering) micro-carriers. They differ in their porosity, specific gravity, optical properties, presence of animal components, and surface chemistries. "Empty" (i.e. cell-free) micro-carriers are then provided in a similar manner as the new medium, i.e. their addition to the cell culture is regulated via the cell density. The micro-carriers can be supplied together as a suspension with the fresh nutrient medium reservoir or from a separate reservoir.

In further embodiments, the optionally harvested cells and/or cell-derived products are further processed. In a first step, the cells may be isolated from the harvested cell culture fraction by centrifugation, filtration/vacuum-filtration or sedimentation. The isolated cells than can be further used for either transient expression systems. In the case of plant cell culture the cells can be used for the transient production process describe in WO2013/113504 A1. In the case of mammalian cell culture the cells can be used for transient expression. The gen delivery for mammalian cells can be done either by viruses (Douglas 2008 Biotechnol Prog) or by chemical agents like inorganic compounds (e.g. Calcium phosphate CaPi, (Jordan and Wurm 2004 Methods)) or cationic polymers (e.g polyethylenimine PEI (Baldi, Hacker et al. 2012 Protein Expression in Mammalian Cells) or cationic lipids (e.g LIPOFECTAMINE®, FUGENE®, 293fectin or by mechanical methods like microinjection or electroporation (Pham, Kamen et al. 2006 Mol Biotechnol).

In some embodiments, a cell-derived product and the cells in the harvested cell culture fraction can be separated by centrifugation and/or filtration and/or sedimentation. Once the Cell culture supernatant is isolated from the cells the supernatant the product will by process furthermore depending of the localization of the product. If the cell-derived product is secreted the product can be purified from the culture supernatant using e.g. chromatography or precipitation methods. If the cell-derived product is intracellular the product has to be extracted from the cells by homogenizing the cells with for e.g. ultrasonic or with the help of a blender or a ball mill. After that the cell fragments can be removed from the cell extract by filtration or centrifugation and the cell extract can be processed further on. The cell extract can be used as product itself. Or the product can be purified from the cell extract using e.g. chromatography or precipitation methods.

In a further embodiment, the process according to the present disclosure comprises at least one growth phase to reach the desired cell density in which no media is added and no fraction of the cell culture is harvested, followed by at least one continuous phase, wherein the cell density is kept essentially constant.

In another embodiment, the process according to the present disclosure comprises an initial growth phase to reach the desired cell density in which no media is added and no fraction of the cell culture is harvested, followed by several, i.e. two or more continuous phases, wherein the cell density is kept essentially constant, and in which the continuous phases are separated by either another growth phase to reach a higher cell density or by a dilution phase to reach a lower cell density.

In another embodiment the process according to the present disclosure comprises a continuous phase in which the cell density is kept constant and which has a duration of more than 48 h, preferably of more than 96 h, more preferably of more than 144 h and most preferably of more than 168 h, and on which 2 or more harvesting steps are performed.

As mentioned above, the process according to the present provides excellent cells for several uses. For example, the produced cells may be used for analytical assays (e.g. metabolism of drugs or other chemical compounds), induction of gene expression (e.g. P450 in liver cells, reporter genes, or any kind further cultivation of the cells combination thereof).

In an advantageous embodiment, the processes and methods according to the present disclosure provide cells that are subsequently used as host cells for transient production. This means that these cells will subsequently transfected/transformed by appropriate means and incubated to produce molecules of interests (products). This is of vital importance for transient production platforms utilizing cell suspensions (both animal and plant cells).

In an advantageous embodiment, the present disclosure pertains to methods for generating a stable cell line comprising the steps of:
i) Cultivating and harvesting cells according to a process of the present disclosure,
ii) Transforming the harvested cells with a nucleic acid to obtain a stable cell line.

In an advantageous embodiment, the present disclosure pertains to methods to execute a gene amplification with e.g. MTX in CHO cells comprising the steps of:
i) Cultivating transfected cells with the process of the present disclosure,
ii) Stepwise increase of the e.g MTX concentration to increase the gen amplification The terms "transformation", "transformed" and "transfected" as used herein relate to the delivery of any nucleic acid or nucleic acid analoga into the produced eukaryotic cells (host cell). After transformation the nucleic acid may be stably integrated into the genome of the host cell.

Alternatively, the delivered nucleic acid may not be integrated into the genome and may exert its effect either in the cytosol or in the nucleus or in any cellular organelle. The nucleic acid may be an autonomously replicating element such as a viroid, a virus or deconstructed virus, or a combination of necessary elements from more than one virus. Alternatively, the delivered nucleic acid may only be a component of an autonomously replicating element such as a viroid, a virus or deconstructed virus. The other components may be provided/complemented by the host cell or by a transgenic host cell.

In some embodiments, the nucleic acid is comprised in a vector, in particular in an expression vector. "Vector" is defined to include, inter alia, any plasmid, cosmid, phage, or viral vector in double or single stranded linear or circular form which may or may not be self transmissible or mobilizable, and which can transform a prokaryotic or eukaryotic host and exists extrachromosomally (e.g. autonomous replicating plasmid with an origin of replication).

"Expression vector" refers to a vector in which a nucleic acid is under the control of, and operably linked to, an appropriate promoter or other regulatory elements for transcription in a host cell such as a microbial or plant cell. The vector may be a bi-functional expression vector which functions in multiple hosts. In the case of genomic or subgenomic DNA, this may contain its own promoter or other regulatory elements and in the case of cDNA this may be under the control of an appropriate promoter or other regulatory elements for expression in the host cell. "Operably linked" means joined as part of the same nucleic acid molecule, suitably positioned and oriented for transcription to be initiated from a promoter.

In an advantageous embodiment, the cells produced with a process of the present disclosure are plant cells and may be used for the generation of plant cell material in the form of a medium-deprived, porous structured and non-tissue multilayer cell pack and for the subsequent maintenance of said cell pack (as described in WO 2013/113504 A1).

Therefore, the present disclosure pertains also to methods for the generation of plant cell material in the form of a medium-deprived, porous structured and non-tissue multilayer cell pack and for the subsequent maintenance of said cell pack, comprising the steps of
(i) providing a cell pack having a porous structure by separating cells from a plant cell suspension culture, wherein the cells were cultivated by a cultivation method according to the present disclosure, and wherein the content of the liquid comprised by the cell pack is reduced and adjusted to correspond to a cell pack density between 0.1 and 0.9 g wet cell weight per $cm^3$, thereby establishing the medium-deprived and porous structured nature of said cell pack, and
(ii) incubating said medium-deprived and porous structured cell pack in a non-liquid environment under a relative humidity of 50 to 100%.

In particular, an advantageous embodiment of the method according to the disclosure comprises (i) a first cultivation step in which a plant cell suspension is cultured according to a cultivation process of the present disclosure, for the provision of a homogeneous plant biomass, (ii) a separation step in which the liquid media is separated from the plant cells in such a way that a porous cell pack with a density between 0.1 and 0.9, preferably between 0.2 and 0.85, most preferably between 0.4 and 0.8 g wet cell weight per $cm^3$ is generated, and (iii) a second cultivation step in which the cell pack is further incubated in a non-liquid environment under controlled conditions (see above) for at least another day. Depending on the actual situation and the practitioner's intent, this second cultivation step may be performed for several days. Typically the second cultivation step is performed for 2 to 7, preferably for 3 to 5 days.

In another embodiment, the processes and methods of the present disclosure are used to produce molecules of interest (as opposed to cells or cell biomass), such as recombinant proteins. In this embodiment, the disclosure potentially provides more homogeneous product of higher quality and maybe also at higher yields as compared to currently established fermentation strategies.

Another embodiment of the present disclosure is the use of the new process to produce recombinant proteins or cell derived products with transgenic cells comprising the steps of:
i) Cultivating and harvesting transgenic cells according to a process of the present disclosure,
ii) Separation of cells from the culture supernatant
iii) Processing of either the culture supernatant (secreted Protein) or
iv) Extraction of the molecule of interest from the cells.

If the cell-derived product is secreted, the product can be purified from the culture supernatant using e.g. chromatography or precipitation methods. If the cell-derived product is intracellular the product has to be extracted from the cells by homogenizing the cells with for e.g. ultrasonic or with the help of a blender or a ball mill. After that the cell fragments can be removed from the cell extract by filtration or centrifugation and the cell extract can be processed further on. The cell extract can be used as product itself. Or the product can be purified from the cell extract using e.g. chromatography or precipitation methods.

Another embodiment of the present disclosure is to produce highly comparable and reproducible cells for the production of components for cell-free systems. For the production of cell free extracts (lysates) for in vitro translation there's a need of large amounts of homogenous starting material/cells. To ensure an optimal productivity of the resultant lysates the cells have to be in an exponential growth phase. In addition the cell density at the point of harvest plays a critical role. Conventionally cell cultures are grown in batch mode to a desired cell density, harvested and immediately processed. This requires a high flexibility in terms of time, as growth rates vary in large fermentation processes making a specific harvest point not precisely predictable. Furthermore an optimal adaption of cells to the culturing process cannot be guaranteed in batch mode. Processing of the cell material to a highly active lysate is another important factor. The established protocols for the production of plant based cell free lysates are often time-consuming and cost-intensive.

Therefore, the present disclosure pertains to methods for the preparation of cell free extract for an in vitro translation comprising the steps of:
i) Cultivating and harvesting cells according to a process of the present disclosure,
ii) Obtaining of a cell-free extract of the cultured cells by subjecting the harvested cells to an extraction treatment using.

As mentioned above, in advantageous embodiments the harvested cells are in an exponentially growing phase.

In further embodiments, the extraction treatment is or comprises an enzymatic treatment. The inventors found that during processing of the cell material to a lysate the costs for protoplastation could be reduced more than hundredfold by replacing conventional enzymes by liquid cellulases and pectinases originally designed for food industry. At the same an improved protoplastation per time unit has been observed. The usage of these enzyme preparations permits the commercial production of the plant-based lysate at usual market prices.

Further modifications to the protocol described by Komoda et al. ((Komoda, Naito et al. 2004 Proc Natl Acad Sci USA)) like altered buffers, wash and centrifugation steps, and the use of a discontinuous instead of a continuous Percoll gradient led to a faster production as well as an easier scalability. An alternative described method of evacuolation of the protoplast was described by Sonobe et al. (Sonobe 1996 J. Plant Res.). Gursinsky et al. (Gursinsky, Schulz et al. 2009 Virology) shows by additional digesting of endogen mRNA with S7-nuclease of the final lysate a highly improved translational activity.

Furthermore, the cells comprised in the harvested cell culture fraction may be also used to inoculate a subsequent fermentation process.

In summary, the cultured and harvested cells according to a process of the present disclosure may be used for performing a subsequent cultivation step, whereby (i) the cells are being transfected/transformed, (ii) gene expression is induced by the addition of an inducer, (iii) the cells are infected, (IV) the cells are cultivated under conditions that favor cell-derived product accumulation, (iv) nucleic acids are transfected into the cells (v), and/or the cells are used for analytical assays.

As mentioned above, the present disclosure pertains to a cell-density regulated cell cultivation process for the production of eukaryotic cells and/or an eukaryotic cell-derived product, wherein the cell density during the cell cultivation is regulated by adjusting the volume of the cell culture comprising the cells and a nutrient medium in a cultivation vessel, said process comprises the following steps:
a) growing the cells in a defined volume of the cell culture,
b) measuring the cell density in the cell culture with a density sensor,
c) regulating the cell density in the cell culture by adding an appropriate volume of the nutrient medium to the cell culture to keep the cells in the growth phase,
d) harvesting a fraction of the cell culture at a desired cell density, wherein the harvested fraction comprises cells and/or a cell-derived product,
e) repeating one or all of the aforementioned steps in the order set forth to allow a repeated harvest of cell culture fractions, and
f) optionally processing the harvested cells and/or cell-derived products, wherein
the eukaryotic cells may be selected from the group consisting of plant suspension cells, insect cells and mammalian cells, and/or
the cell-derived product may be a primary or secondary metabolite or a recombinant protein like an enzyme, an antibody, an antibody fragment, a vaccine, a cytokine, a hormone, a peptide or a virus or a virus like particle or a nucleic acid, and/or
the cell culture may be added into the cultivation vessel as a starter culture, and/or
the density sensor may be selected from the group consisting of sensor based on turbidity measurements, laser scatter measurements, NIR measurements or capacitive measurements or at line systems like cell counter or any other methods which measure cell density and allow for feedback-control, and/or
the cell density in the cell culture may be measured continuously, and/or
the appropriate volume of the nutrient medium may be transferred into the cell culture in the cultivation vessel from at least one nutrient medium reservoir, and/or
the cell density may be regulated by using a control loop comprising a sensor continuously measuring the cell density (input signal) and a controller generating an output signal that triggers a pump/or valve or adding the appropriate volume of the nutrient medium to the cell culture, and/or
the cell density in the cell culture may be regulated to be constant over time or to be a specific time-dependent function for the cell density, and/or
the cultivation vessel may be operated between a minimal and a maximal cell culture filling level, and/or
any volume fractions within the min/max range of the fermentation culture may be harvested from the cultivation vessel, and/or
a fraction of the cell culture may be harvested when the cells are in an exponentially growing phase, and/or
(i) at least one additional cultivation vessel may be connected to the first cultivation vessel to increase the cultivation volume, (ii) the cell density in each connected cultivation vessel may be the same and (iii) the cell culture may be exchanged between the cultivation vessels, and/or the cells may be cultivated in the presence of microcarriers, and/or the cells may be isolated from the harvested cell culture fraction, and/or the cell-derived product and the cells in the harvested cell culture fraction may be separated by centrifugation and/or filtration and/or sedimentation, and/or the cells comprised in the harvested cell culture fraction may be used to inoculate a subsequent fermentation process, and/or the harvested cells may be used for performing a subsequent cultivation step, whereby (i) the cells being transfected/transformed (ii), gene expression is induced by the addition of an inducer, (iii) the cells are infected, (IV) the cells are cultivated under conditions that favor cell-derived product accumulation, (iv) nucleic acids are transfected into the cells (v), and/or the cells are used for analytical assays, and/or the cells may be used to prepare cell-free extracts, and/or Furthermore, the present disclosure pertains to a method for the preparation of cell free extract for an in vitro translation comprising the steps of:
  i) Cultivating and harvesting cells according to an aforementioned process,
  ii) Obtaining of a cell-free extract of the cultured cells by subjecting the harvested cells to an extraction treatment using, wherein
  the harvested cells may be in an exponentially growing phase, and/or
  the extraction treatment may comprise an enzymatic treatment, and/or
  the enzymatic treatment may comprise a cellulose and pectinase treatment, and/or
  the cell lysate may be centrifuged to obtain its supernatant to prepare the cell-free extract.

Furthermore, the present disclosure pertains to a method for generating a stable cell line comprising the steps of:
  i) Cultivating and harvesting cells according to an aforementioned process,
  ii) Transforming the harvested cells with a nucleic acid to obtain a stable cell line.

Furthermore, the present disclosure pertains to a method for the generation of plant cell material in the form of a medium-deprived, porous structured and non-tissue multilayer cell pack and for the subsequent maintenance of said cell pack, comprising the steps of
  (i) providing a cell pack having a porous structure by separating cells from a plant cell suspension culture, wherein the cells were cultivated by a method according to any one of claims 1 to 17, and wherein the content of the liquid comprised by the cell pack is reduced and adjusted to correspond to a cell pack density between 0.1 and 0.9 g wet cell weight per $cm^3$, thereby establishing the medium-deprived and porous structured nature of said cell pack, and
  (ii) incubating said medium-deprived and porous structured cell pack in a non-liquid environment under a relative humidity of 50 to 100%.

Figure 9:
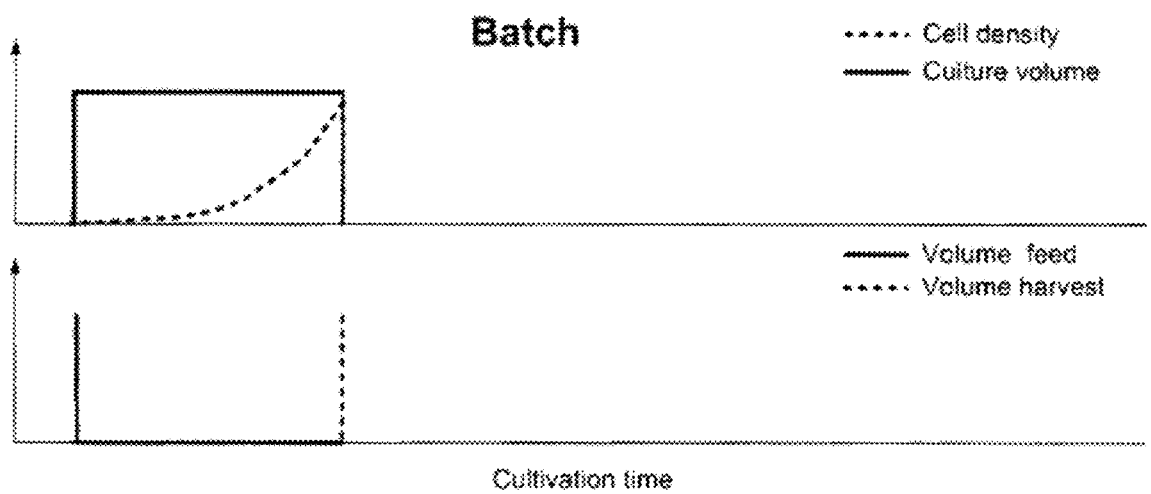
FIG. 9 shows two diagrams A) the culture volume, cell density, feed rate and harvest rate during the cultivation time in a batch fermentation process and B) the culture volume, cell density, feed rate and harvest rate during the cultivation time in a fed batch fermentation process.
Figure 9:
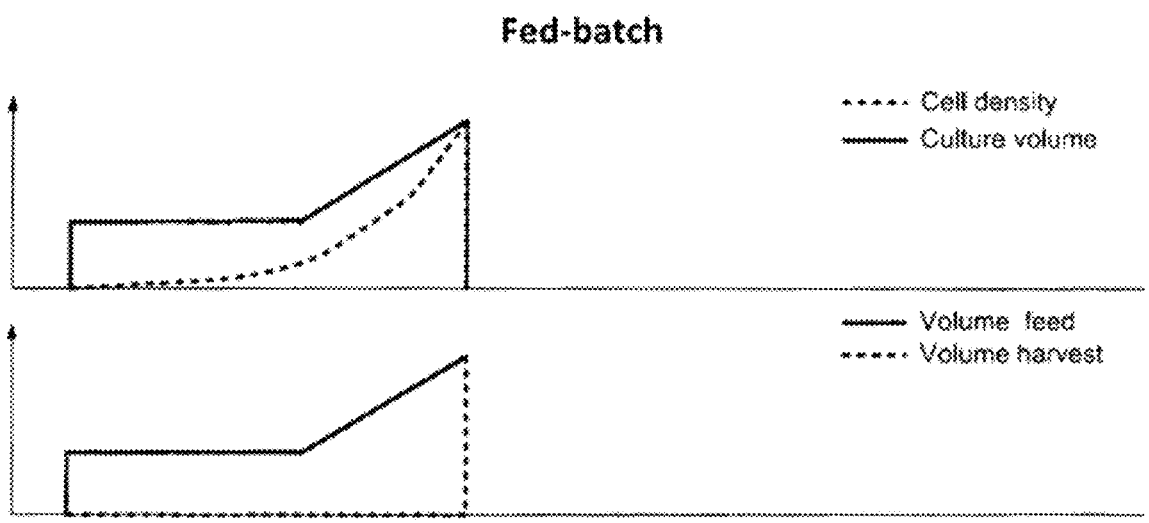
Figure 10:
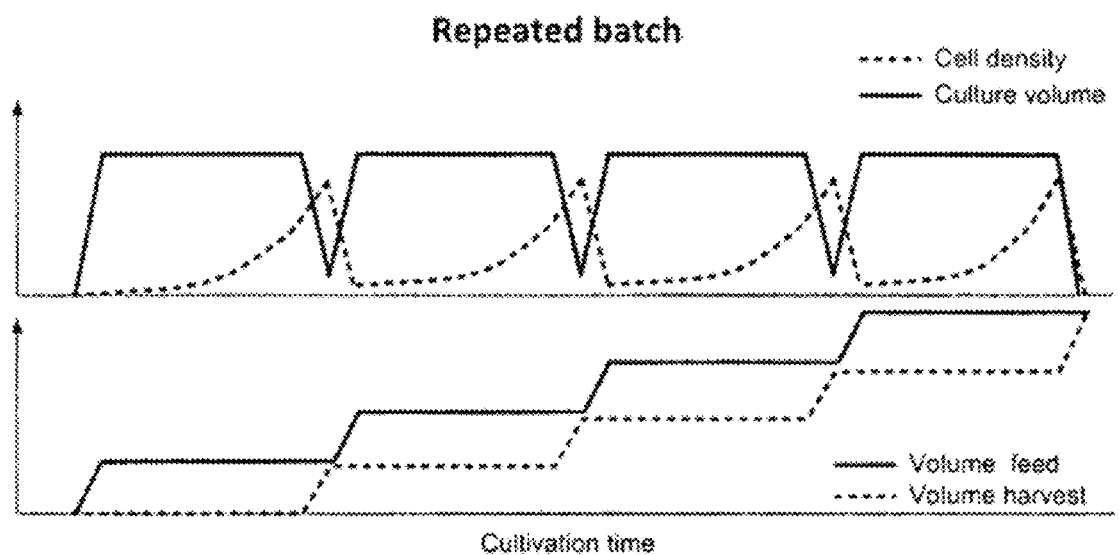
FIG. 10 shows two diagrams A) the culture volume, cell density, feed rate and harvest rate during the cultivation time in a repeated batch fermentation process and B) the culture volume, cell density, feed rate and harvest rate during the cultivation time in a continuous chemo-/turbidostat fermentation process.
Figure 10:
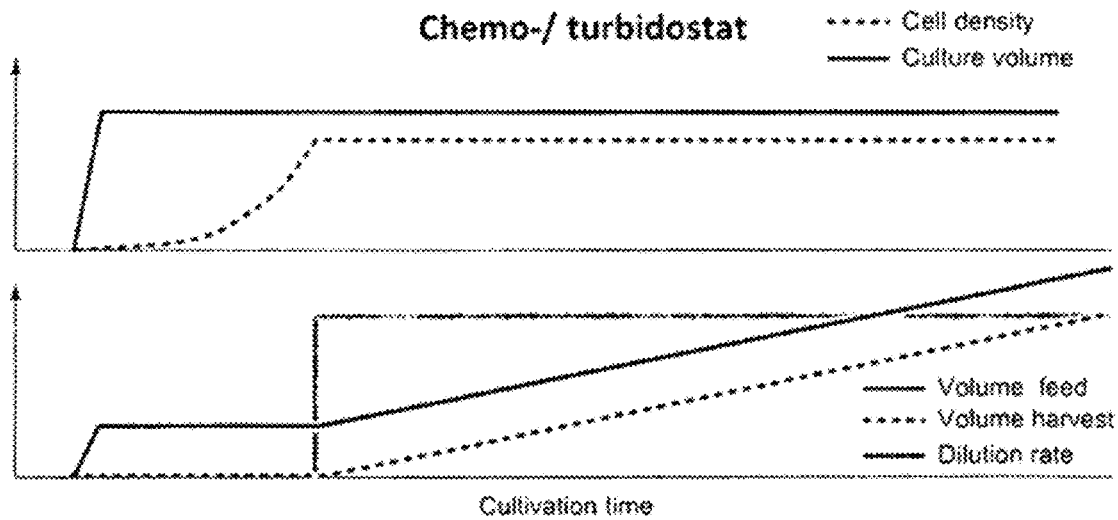
Figure 11:
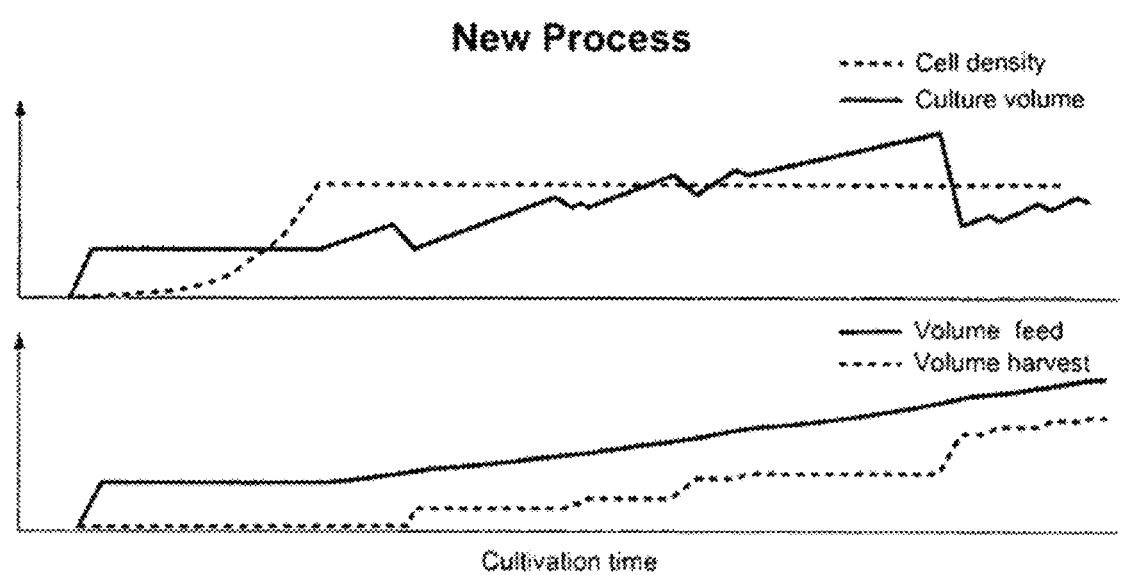
FIG. 11 is a diagram showing the characteristics of a fermentation process according to the present disclosure in view of culture volume, cell density, feed rate and harvest rate during the cultivation time.

FIGS. 9, 10 and 11 show the different fermentation processes, whereby the processes can be distinguished by comparing the culture volume, cell density, feed rate and harvest rate. In the mentioned Figures the cell density is defined the number of cells per mL in the culture or parameter that can be transformed or related to that number, the culture volume is defined as the volume of the fermentation broth in the bioreactor, the volume feed is defined as the accumulated volume of media that is added into the bioreactor over the process, the volume harvest is defined as the accumulated volume of fermentation broth removed from the bioreactor over the process, the feed rate is defined as the volume of media added to the bioreactor per time unit (e.g. mL/min), the harvest rate is defined as the volume of fermentation broth removed from the bioreactor per time unit (e.g. mL/min), and the dilution rate equals the feed rate and the harvest rate for the chemo-/turbidostat.

In an advantageous embodiment, the process according to the present disclosure is carried out in a 7 L vessel, the configuration of the sensors and impeller requires that the minimal volume is 1 L, the maximal volume is 6 L as e.g. stated by the manufacturer, and the cultivated cells have a doubling time of 24 h.

In a first example, the actual volume ("fill level") is 4 L. The operator can e.g. harvest 3 L at once and process the entire harvest without the need to collect it over extended periods of time (this is also cold a collection or hold step), as e.g. necessary in the chemo-/turbidostat processes.

Alternatively, the operator can also decide to harvest 100 mL to e.g. measure the cell viability or other parameters of the cell culture, or perform a small-scale experiment, and then subsequently harvest 2.9 L for further processing.

In a second example, the fill level is 6 L. The operator harvests 3 L and e.g. uses the cells for subsequent transient gene expression experiments. On the next day in the morning, the actual volume has e.g. reached 5 L due to culture growth and proportional addition of fresh media. The operator can now again harvest 3 L, perform the same experiment, and can be sure that the cells harvested from the culture have the same properties (e.g. cell density, viability and other performance properties such as transfection efficiency). This is in contrast to cells harvested from a batch or fed-batch process. In the evening, the actual volume is e.g. 2.6 L, the operator harvests 1 L, and can again be sure that the cells harvested from the culture have the same properties.

In a third example, the actual volume is 4 L and the cells are used for generation of a cell-free extract that is used for in-vitro translation. On this day, several researchers decided to perform such experiments but none of them has planned ahead and ordered cells from the cell culture unit. At 9:30 the first researcher harvests 1 L of fermentation broth, the second researcher harvests another 2 L just ten minutes later. At the same time a third researcher requests just another 250 mL but needs to wait a bit until the actual culture volume has reached 1.25 L.

If the culture volume reaches the maximal volume, fermentation broth needs to be removed either automatically or manually. Again the volume that is removed can freely be chosen to be within the range of the maximal volume minus the minimal volume. It is a particular feature of the invention that the harvest volume can be chosen such that the process will yield a desired volume of culture broth in the future, e.g. the afternoon, next day or after the weekend. And again, the harvested fermentation broth is highly reproducible.

These examples clearly show that work flows can be optimized by allowing flexible harvesting and by giving the operator the possibility to adjust the timing of the harvest time point through deliberate placing of previous harvests (which can either be used or be discarded). Thereby, the process according to this invention can easily be adjusted to subsequent steps, which results in a higher overall flexibility and robustness. This enables a better usage of the production facility.

The following examples are given to further illustrate the present invention without being deemed limitative thereof.

METHODS AND EXAMPLES

In the following examples, materials and methods of the present disclosure are provided. It should be understood that these examples are for illustrative purpose only and are not to be construed as limiting this disclosure in any manner. All publications, patents, and patent applications cited herein are hereby incorporated by reference in their entirety for all purposes.

1.) Cultivation of BY-2 Plant Suspension Cells in a 7-L Stirred Tank Bioreactor

The cultivation was carried out at 26° C. in an autoclaveable 7-L stirred tank bioreactor (Applikon, Schiedam, the Netherlands). The bioreactor was filled with a minimal volume of 1.5 L of a modified MS-medium (Murashige and Skoog, 1962; MS-salts 4.3 g/L, myoinositol 100 mg/L, $KH_2PO_4$ 200 mg/L, HCl-Thiamin 1 mg/L, 2,4-Dichlorophenoxyacetic acid 0.2 mg/L, sucrose 30 g/L) and inoculated with a 6-day-old preculture of BY-2 cells. Pluronic L-61 (BASF, Mount Olive, N.J.) was added at a concentration of 0.01% (v/v) to control foaming and wall growth. The fermentation was controlled using an ez-control (Applikon) and BioXpert XP was used to collect the online data. The reactor was aerated with constant flow rate of 0.5 L/min. Dissolved oxygen concentration ($dO_2$) was controlled to a saturation of 30% by regulating the stirrer speed. The pH was monitored but not controlled. Viable online biomass was measured using the FUTURA® RFIS system (Aber Instruments, Aberystwyth, UK). The permittivity of the cells and conductivity of the medium were measured simultaneously using an annular electrode (12×120 cm) and a standard remote FUTURA® instrument operating in cell culture mode at 0.6 MHz with polarization correction. The biomass sensor was controlled with FUTURA® software. The minimal working volume of this bioreactor was 1.5 L, which was required to have all sensors in appropriate contact with the cell culture to ensure proper measurement and to have adequate mixing. The maximal working volume was 5.5 L. The harvest was either carry out manually or by an automated harvest procedure. Therefore the output signal of a level sensor, which was fixed at the filling volume of 5.5 L, was used to switch on an external pump. BioExpert was used to record the output signal of the level sensor and to remote control the external pump with a programed phase within the fermentation recipe. The programmed phase defined the harvest volume based on the running time of the pump. The harvest tube was connected to the external pump when the reactor was left unattended (i.e. during the weekend). Whenever the filling volume reached 5.5 L and thus contacting the level probe, a starting signal for the external pump was generated. In that experiment a defined volume of 1 L of suspension was pumped out of the reactor. This control loop served as a safety measure to avoid the need of a regular supervision of the fermentation and to prevent the overflow of the reactor when it was left unattended.

After inoculation and the initial lag-phase the cells entered the exponential growth phase. With a specific growth rate of 0.029 $h^{-1}$ for the exponential growth phase the suspension reached a biomass concentration of 100 g/L fresh weight after 116 h of cultivation. The process value for the permittivity measurement was fixed as a set point. Further in the cultivation process the actual process values were compared to that corresponding permittivity set point in intervals of 5 s. In the beginning of this continuous growth phase the permittivity set point was adjusted at different time points, as the offline measured fresh weight was below 100 g/L. A PID (proportional integral differential) controller was used for process control and a pump was used as an actuator that transformed the controller output into an actuator output. In this case the actuator output was a certain volume of fresh medium that was added to the bioreactor depending on the offset of the process value, the PID settings and the tubing used for media addition. The addition of fresh medium from a tank into the bioreactor resulted in the dilution of the fermentation broth and a decrease of the permittivity, thus adjusting the process value to the set point. After the initial batch-phase was intercepted, by starting the biomass control, the cultivation and biomass production continued for another 64 days yielding a total of 88 L suspension and 8.8 kg cells. During 1200 h of cultivation the process allowed to harvest variable volumes (0.01 L-4.0 L) at different time points with different intervals (36 harvests in total). Because the collection of online data was interrupted after a process time of 1200 h the FIG. 2 and the table 1 only display data for this period.

Figure 2:
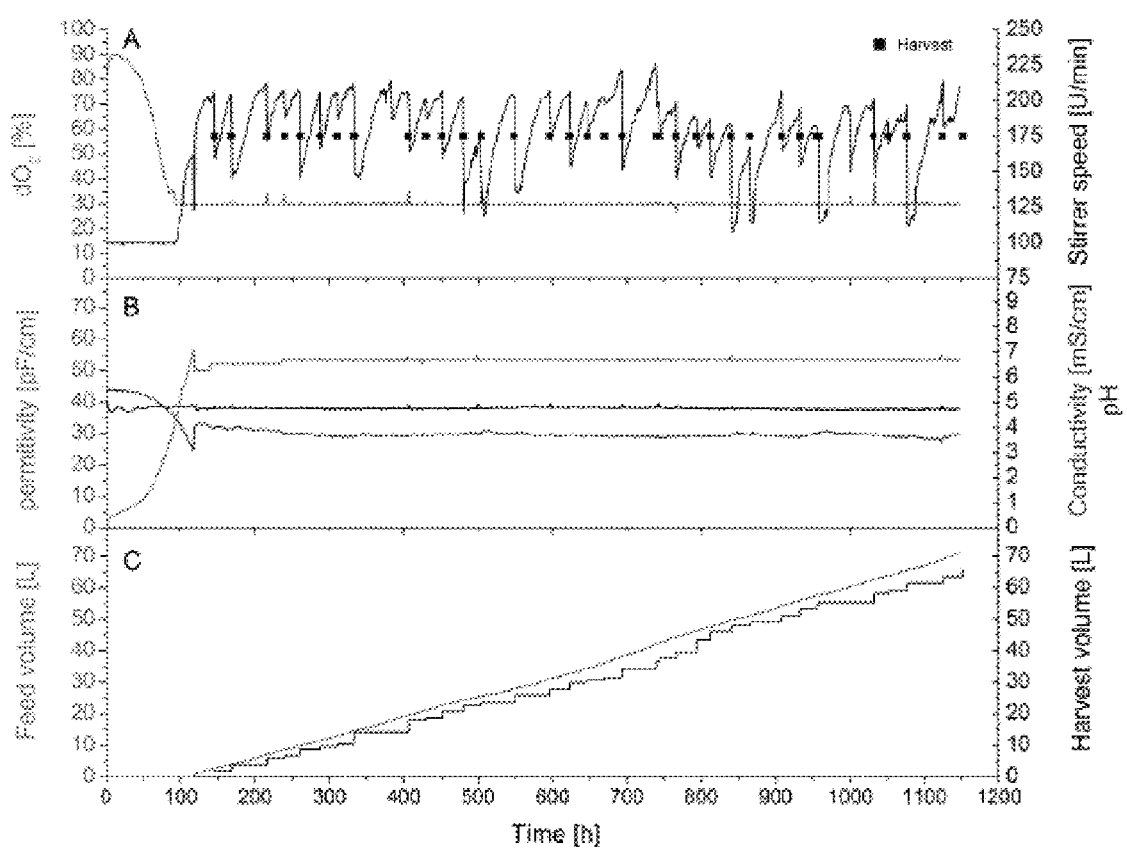
FIG. 2 is a diagram showing online data for the semi-continuous cultivation of tobacco BY-2 cells.

FIG. 2 shows the cultivation of tobacco BY-2 cells with the novel cultivation strategy. A: Course of the oxygen concentration, the stirrer speed and the documented harvests (■) during the cultivation process. B: Developing of process values for conductivity, pH and the permittivity (biomass concentration). C: Course of the medium addition during the continuous process phase. With the feed volume representing the online data for the medium addition and the harvest volume for the offline documented harvests.

Table 1 shows the different variable harvest volumes at different times during the fermentation process and the accumulated harvest volume over the entire process. For example, a volume 0.6 L was harvested at 430.1 h (Table 1, Harvest No. 11), whereas a volume of 3.2 L was harvested at 793.2 h (Table 1, Harvest No. 24).

The shortest time between two consecutive harvest points was 3.6 h (Table 1 Harvest No. 30-31), whereas the longest time between two harvest time points was 73.7 h (Table 1 Harvest No. 31-32). Between the fermentation times from 310.4 h to 334 h three individual harvest with different volumes have been conducted (Table 1; Harvest No. 7-9). This clearly demonstrates that the harvest volume and the harvest time interval are highly flexible thus enabling a harvest on demand.

TABLE 1

Documentation of harvests conducted during the cultivation

| Harvest No. | Process time [h] | Harvest volume [L] | Total harvest volume [L] |
|---|---|---|---|
| 1 | 145.4 | 1.8 | 1.8 |
| 2 | 168.8 | 2 | 3.8 |
| 3 | 215.8 | 1.8 | 5.6 |
| 4 | 240 | 1 | 6.6 |
| 5 | 260.7 | 2 | 8.6 |
| 6 | 287.1 | 1 | 9.6 |
| 7 | 310.4 | 0.8 | 10.4 |
| 8 | 333 | 1 | 11.4 |
| 9 | 334 | 2.6 | 14 |
| 10 | 406 | 4 | 18 |
| 11 | 430.1 | 0.6 | 18.6 |
| 12 | 451.6 | 2 | 20.6 |
| 13 | 479.8 | 1.8 | 22.4 |
| 14 | 503.9 | 1 | 23.4 |
| 15 | 548.4 | 2.4 | 25.8 |
| 16 | 596.1 | 2 | 27.8 |
| 17 | 623.5 | 2 | 29.8 |

TABLE 1-continued

Documentation of harvests conducted during the cultivation

| Harvest No. | Process time [h] | Harvest volume [L] | Total harvest volume [L] |
|---|---|---|---|
| 18 | 646.7 | 0.8 | 30.6 |
| 19 | 669.7 | 0.7 | 31.3 |
| 20 | 693.5 | 3 | 34.3 |
| 21 | 739 | 2 | 36.3 |
| 22 | 743.7 | 1 | 37.3 |
| 23 | 765.8 | 2 | 39.3 |
| 24 | 793.2 | 3.2 | 42.5 |
| 25 | 811.9 | 2.6 | 45.1 |
| 26 | 839.4 | 2 | 47.1 |
| 27 | 865 | 1 | 48.1 |
| 28 | 907.9 | 2 | 50.1 |
| 29 | 932.3 | 2 | 52.1 |
| 30 | 954.5 | 1 | 53.1 |
| 31 | 958.1 | 1 | 54.1 |
| 32 | 1031.8 | 2 | 56.1 |
| 33 | 1050.9 | 0.6 | 56.7 |
| 34 | 1076.4 | 2.5 | 59.2 |
| 35 | 1124.3 | 2 | 61.2 |
| 36 | 1151.5 | 2.6 | 63.8 |

Figure 3:
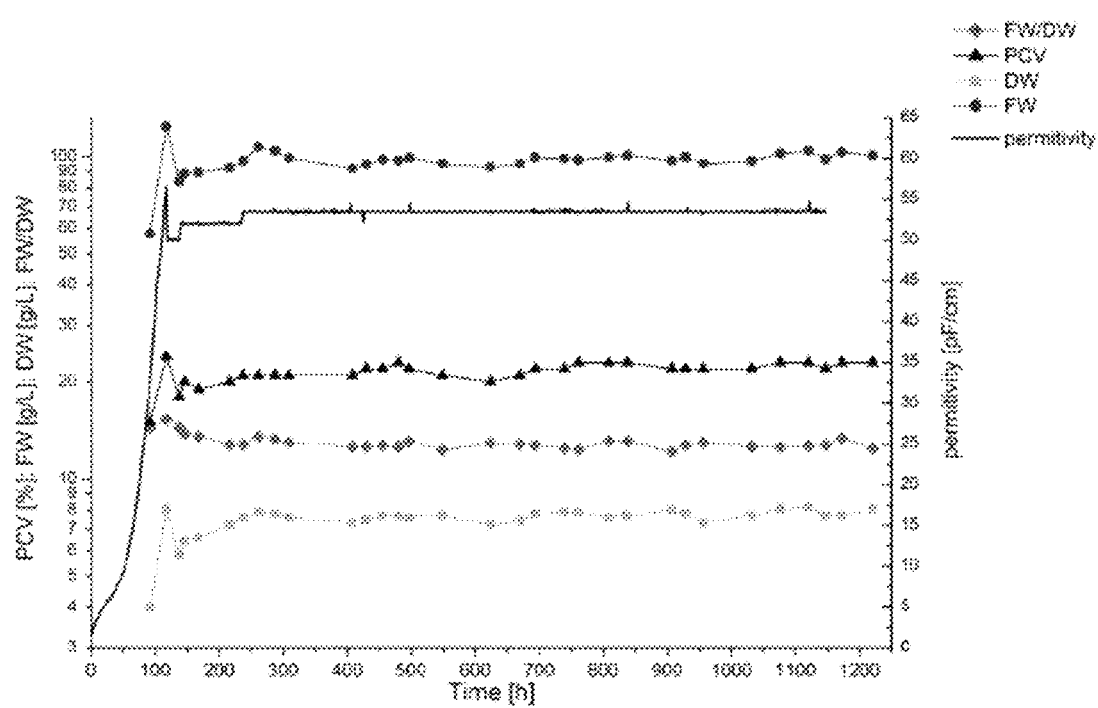
FIG. 3 is a diagram showing offline parameter for the semi-continuous cultivation of tobacco BY-2 cells.

During the production phase cells were growing exponentially with the same specific growth rate of 0.029 $h^{-1}$, which was determined during the exponential growth phase. Furthermore the online signals for $dO_2$, pH, conductivity and permittivity stayed constant after starting the control loop throughout the process, thus demonstrating the robustness of the process. Especially the permittivity was not only constant considering the online signal but also in terms of actual biomass concentrations, which were measured offline by determining the offline parameters of packed cell volume (PCV), dry weight and fresh weight. The comparison of the online and offline parameters showed excellent agreement between both methods (FIG. 3).

2.) Production and Screening by Transient Expression in Plant Cells

A newly developed procedure for the high-throughput screening of expression constructs using tobacco BY 2 plant cell packs (PCPs) (Patent No. WO 2013/113504 A1), was compared to standard agroinfiltration of leaves. Tobacco BY-2 cells cultivated with the novel cultivation strategy were transferred to 96-well receiver plates and 96-well PCPs with a fresh weight of ~200 mg were generated simultaneously by applying a vacuum. The PCPs were transfected by adding 200 mL A. tumefaciens strain GV3101 suspension at $OD_{600}$=0.1. Three bacterial cultures were used, each carrying the expression constructs for one of the three antibodies, thus generating 32 PCPs transfected with each construct. After incubation for 30 min, the suspension was removed by vacuum filtration to regenerate the porous PCPs. For transient gene expression, the receiver plate containing the PCPs was incubated at 26° C. and 50% humidity in a phytochamber for 5 days. At the same, 4-week-old Nicotiana tabacum K326, N. tabacum SR-1 and N. benthamiana plants were infiltrated with A. tumefaciens suspension (OD600=1) derived from the same cultures used for the PCPs. Four leaves (different ages) on each plant were injected with bacteria and the plants were incubated for 5 days at 23° C. with a 16-h photoperiod. Total soluble protein was extracted from the PCPs and leaves, and the concentrations of the three antibodies were compared by surface plasmon resonance spectroscopy (FIG. 4).

Figure 4:
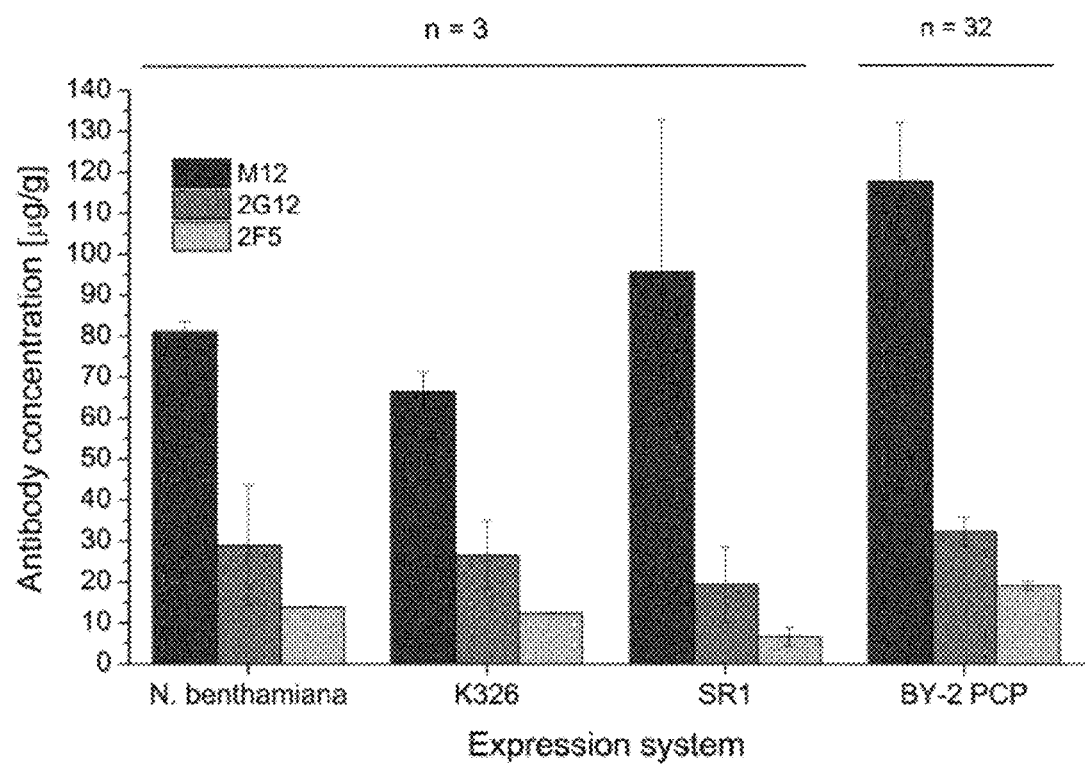
FIG. 4 is a diagram showing the comparison of different whole-plant expression systems (*N. benthamiana*, *N. tabacum* K326 and *N. tabacum* SR-1) with tobacco BY-2 PCPs for the screening of transient gene expression (presented as antibody accumulation) 5 days after *Agrobacterium*-mediated gene transfer.

FIG. 4 shows the comparison of different whole-plant expression systems (N. benthamiana, N. tabacum K326 and N. tabacum SR-1) with tobacco BY-2 PCPs for the screening of transient gene expression (presented as antibody accumulation) 5 days after Agrobacterium-mediated gene transfer. The antibody concentrations were determined by SPR spectroscopy.

The comparison showed that the different transient expression methods produce comparable results in terms of relative antibody yields, therefore showing that the PCPs can predict the activity of expression constructs in whole plants. The PCP method was also characterized by a much lower coefficient of variation for antibody accumulation while achieving the highest concentrations for all three antibodies, including a three-fold increase in the accumulation of 2F5 (Table 2).

The newly developed cultivation strategy states a perfect method to supply plant cell biomass for the demand of a high-throughput screening platform with plant cell packs. Furthermore it ensures the repeatability of a screening by continuously generating plant cell biomass of a comparable quality.

TABLE 2

Quantification of antibody concentrations in extracts from the different expression systems 5 days after infiltration (BY-2 PCP n = 32, plant species n = 3)

| Expression system | BY-2 PCP | N. tabacum SR1 | N. tabacum K326 | N. benthamiana |
|---|---|---|---|---|
| M12 [µg/g] | 117.9 ± 14.4 | 95.7 ± 37.3 | 66.5 ± 4.8 | 81.2 ± 2.3 |
| 2G12 [µg/g] | 32.3 ± 3.5 | 19.3 ± 9.3 | 26.5 ± 8.4 | 28.9 ± 14.7 |
| 2F5 [µg/g] | 19.0 ± 1.1 | 6.7 ± 2.3 | 12.3 ± 0.1 | 13.8 ± 0.2 |

3.) Production of Cell Free Extracts (Lysates) For In vitro Translation

In an experimental arrangement the productivity of lysates prepared from Tobacco Bright Yellow 2 (BY-2) cells grown in batch cultures was compared to those grown in a continuous fermentation. In each case one liter of BY-2 cell culture with a packed cell volume of 20% was simultaneously subjected to the modified protocol for lysate preparation according to Komoda et al. (2004).

In each case one liter of BY-2 cell culture grown in Murashige and Skoog liquid culture (Murashige and Skoog Basal Salt Mixture, Duchefa Biochemie, Haarlem, Niederlande) supplemented with 3% (w/v) sucrose, 1 mg/L Thiamine hydrochloride, 0.2 mg/L 2,4 dichlorophenoxyacetic acid and 100 mg/L myo-inositol was centrifuged at 250×g for 5 min. The cell pellet was resuspended in three volumes of protoplastation buffer consisting of 3.6 g/L Kao and Michayluk medium (Duchefa Biochemie), 0.36 M Mannitol, 3% (v/v) Rohament CL, 2% (v/v) Rohament PL und 0.1% (v/v) Rohapect UF (all from AB Enzymes, Darmstadt, Germany) as well as the phytohormones NAA (α-naphthalic acid 0.5 µg/mL) und BAP (6-benzylaminopurine 1 µg/mL). A pH of 5 was adjusted with potassium hydroxide. The suspension was incubated at 27° C. and 70 rpm for 1.5 h. After protoplastation the suspension was centrifuged at 110×g for 5 min and the resulting cell pellet was directly applied to a discontinuous Percoll gradient consisting of (from top to bottom) 3 mL 0%, 3 mL 15%, 5 mL 30%, 5 mL 40% and 3 mL 70% Percoll (GE Healthcare, Munich, Germany) in 0.7 M mannitol, 20 mM $MgCl_2$, and 5 mM PIPES-KOH (pH 7.0). After centrifugation at 12.000×g for 1 h evacuolated protoplasts (so-called mini protoplasts) were recovered from the interface between the 40% and 70% Percoll layers and washed in 0.7 M mannitol at 100×g for 5 min. The mini protoplasts were resuspended in three volumes of TR buffer (30 mM HEPES-KOH, pH 7.4, 80 mM potassium acetate, 0.5 mM magnesium acetate, 2 mM DTT and one tablet per 50 mL of Complete EDTA-free protease inhibitor mixture (Roche Diagnostics, Mannheim, Germany)). Subsequently the mini protoplasts were disrupted in a nitrogen decompression chamber (Parr Instrument, Frankfurt, Germany) at 10 bar for 30 min. The nuclei and membrane fragments were removed by centrifugation at 500×g and 4° C. for 10 min. After addition of 0.5 mM $CaCl_2$ and 75 U/mL nuclease S7 (Roche Diagnostics) the supernatant was incubated at 20° C. for 15 min. The lysate was supplemented with 1 mM EGTA, frozen in liquid nitrogen and stored at −80° C. in 1 mL aliquots.

Figure 5:
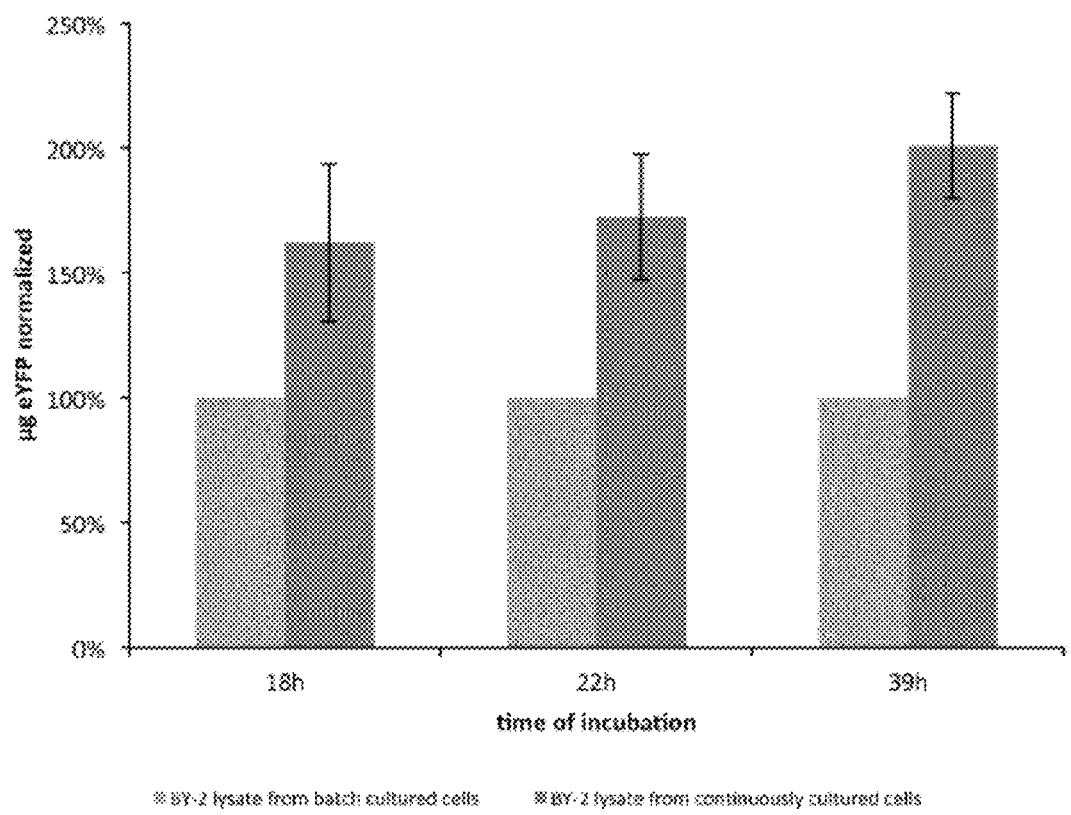
FIG. 5 is a diagram showing the comparison of the yield of enhanced yellow fluorescent protein (eYFP) produced in a coupled transcription/translation cell free tobacco BY-2 system, which was prepared from batch cultured cells and from continuous cultured cells, respectively.

Concerning the concentrations of reaction components the resulting lysates were optimized by a design of experiments (DoE) approach to a maximal in vitro translational activity. With the lysate obtained from the continuously fermented cells a 100% higher translational activity has been observed in comparison with the lysate prepared from cells cultured in batch mode (FIG. 5). Also the absorption at 260 nm as an indicator for the concentration of ribosomes and the resulting higher productivity was higher in the lysates obtained from the continuously fermented cells (+20-25%).

In uncoupled (mRNA as a template) as well as coupled (plasmid DNA as template) batch mode the productivity of the BY-2 lysate is almost twice as high as commercially available plant-based systems (wheat germ extract).

FIG. 5 shows a comparison of the yield of enhanced yellow fluorescent protein (eYFP) produced in a coupled transcription/translation cell free Tobacco BY-2 system, which was prepared from batch cultured cells and from continuous cultured cells, respectively. As shown in the graphs a >100% increase in translational activity could be achieved from the continuous cultured cells derived lysate compared to the batch derived lysate. Incubation was performed at 25° C. and 750 rpm for up to 39 h.

Figure 6:
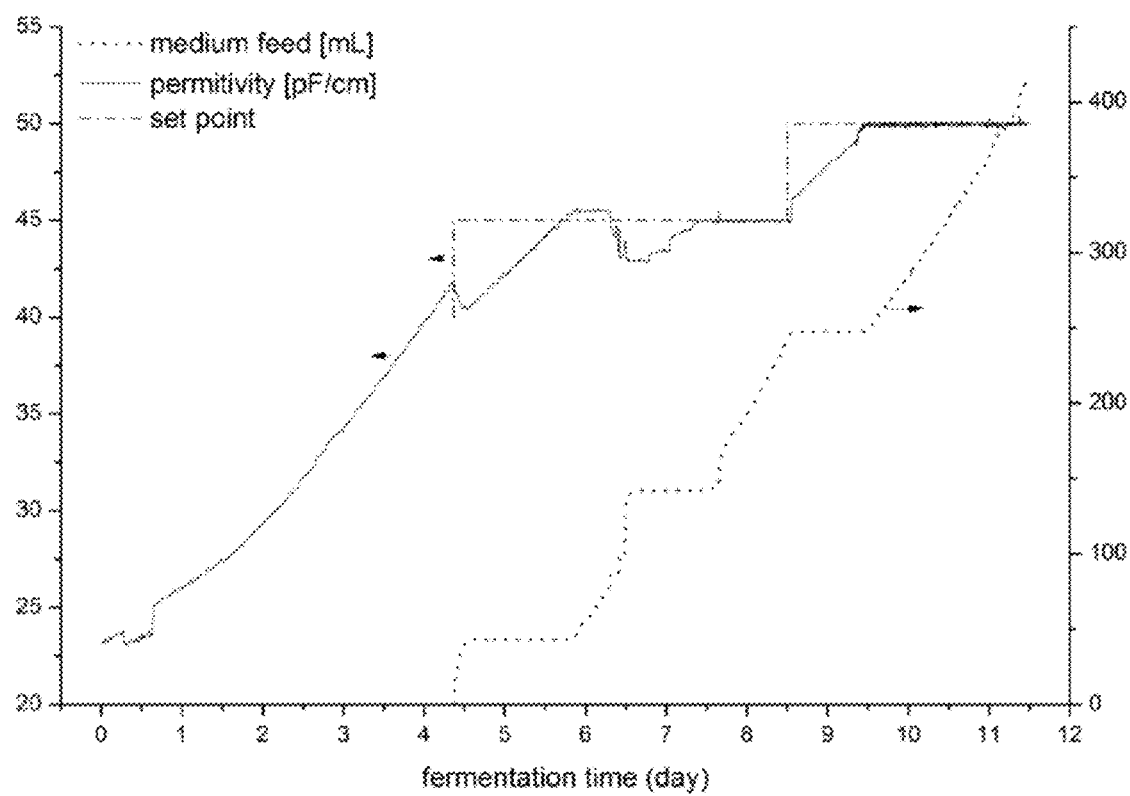
FIG. 6 is a diagram showing online data for the semi-continuous cultivation of *Sorbus torminalis* cells

4.) Cultivation of a Sorbus torminalis suspension culture (Elsbeere) in a 3-L stirred tank bioreactor. The cultivation was carried out at 26° C. in an autoclaveable 3-L stirred tank bioreactor (Applikon, Schiedam, The Netherlands). The bioreactor was filled with 2 L MS-medium (Murashige and Skoog, 1962; MS-salts 4.3 g/L, myoinositol 100 mg/L, KH2PO4 200 mg/L, HCl-Thiamin 1 mg/L, 2.4-Dichlorophenoxyacetic acid 0.2 mg/L, sucrose 30 g/L) and inoculated with a 6-day-old pre-culture of Sorbus torminalis cells. Pluronic L-61 (BASF, Mount Olive, N.J.) was added at a concentration of 0.01% (v/v) to control foaming and wall growth. Dissolved oxygen concentration (dO2) was maintained at a 20% Set point of saturation by automatically pulsing pressurized air into the fermenter using a sintered metal sparger at an aeration rate of 0.1 vvm. The fermentation was controlled using an ez-control (Applikon) and BioXpert XP was used to collect the online data. The pH was monitored but not controlled. Viable online biomass was measured using the Futura RFIS system (Aber Instruments, Aberystwyth, UK). The permittivity of the cells and conductivity of the medium were measured simultaneously using an annular electrode (12×120 cm) and a standard remote Futura instrument operating in cell culture mode at 0.6 MHz with polarization correction. The biomass sensor was controlled with Futura software. The process value for the permittivity measurement was fixed at different set points during the fermentation process (40 pF/cm 0-4.5 dpi; 45 pF/cm 4.5-8.5 dpi; 50 pF/cm from 8.5-11.5 dpi). In the cultivation process the actual process values were compared to that corresponding permittivity set point in intervals of 5 s. A PID controller was used for process control. The specific setting of the P, I and D parameters were P-gain=20, I-time=0 and D-time=0. An Actuator transformed the controller output into an actuator output. When the permittivity signal exceeded the set point a pump was controlled to add new sterile medium from a medium tank into the bioreactor, thus diluting the medium and reducing the permittivity to the value of the set point. FIG. 6 clearly shows that not only N. tabacum cv. BY-2 cells are suited for the fermentation strategy also suspension cells cultures from Sorbus torminalis have successfully been cultivated. During the first 4 days of the fermentation the cells were in the batch phase and reached the set point of 40 pF/cm for the first time. At 4,5 days post inoculation that the set point was increased to 45 pF/cm. The cells needed approximately one day to reach this set point. The set point was fixed at 45 pF/cm for approximately 4 days. In between these 3 days a total of 200 mL of suspension could be harvested. After 8.5 days post inoculation the set point was again increased to 50 pF/cm and the cells reached this biomass again after approximately one day. The fermentation was operated for additional 3 days. In total approximately 400 mL cell suspension could be harvested in 11.5 days.

5.) Cultivation of a Pyrus communis Suspension Culture (Birne) in a 3-L Stirred Tank Bioreactor The cultivation was carried out at 26° C. in an autoclaveable 3-L stirred tank bioreactor (Applikon, Schiedam, The Netherlands). The bioreactor was filled with 2 L MS-medium (Murashige and Skoog, 1962; MS-salts 4.3 g/L, myoinositol 100 mg/L, KH2PO4 200 mg/L, HCl-Thiamin 1 mg/L, 2.4-Dichlorophenoxyacetic acid 0.2 mg/L, sucrose 30 g/L) and inoculated with a 6-day-old pre-culture of Sorbus torminalis cells. Pluronic L-61 (BASF, Mount Olive, N.J.) was added at a concentration of 0.01% (v/v) to control foaming and wall growth. Dissolved oxygen concentration (dO2) was maintained at a 20% Set point of saturation by automatically pulsing pressurized air into the fermenter using a sintered metal sparger at an aeration rate of 0.1 vvm. The fermentation was controlled using an EZCONTROL® (Applikon) and BIOXPERTXP® was used to collect the online data. The pH was monitored but not controlled. Viable online biomass was measured using the FUTURA® RFIS system (Aber Instruments, Aberystwyth, UK). The permittivity of the cells and conductivity of the medium were measured simultaneously using an annular electrode (12×120 cm) and a standard remote FUTURA® instrument operating in cell culture mode at 0.6 MHz with polarization correction. The biomass sensor was controlled with FUTURA® software. The process value for the permittivity measurement was fixed at different set-points during the fermentation process Further in the cultivation process the actual process values were compared to that corresponding permittivity set-point in intervals of 5 s. A PID controller was used for process control. The specific setting of the P, I and D parameters were P-gain=20, I-time=0 and D-time=0. An Actuator transformed the controller output into an actuator output. When the permittivity signal exceeded the setpoint a pump was controlled to add new sterile medium from a medium tank into the bioreactor, thus diluting the medium and reducing the permittivity to the value of the set-point.

The fermentation strategy was used to cultivated suspension cells lines from Pyrus communis. The effect of a stepwise increase or decrease of the permittivity set point within the process should be investigated.

Figure 7:
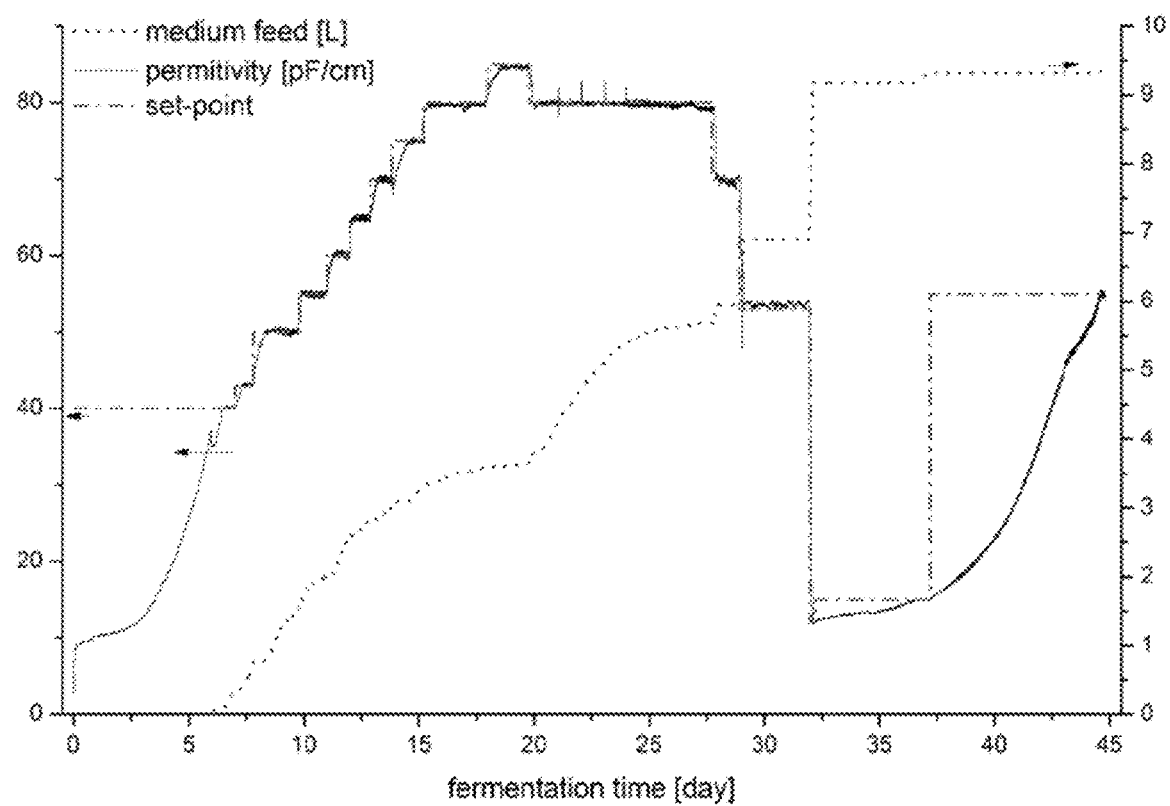
FIG. 7 is a diagram showing online data for a semi-continuous cultivation of *Pyrus communis* cells.

In the FIG. 7 the "dot-line-dot" line shows the set point changes over the entire process. The first set point of 40 pF/cm was reached after 6 days past inoculation (dpi) and afterwards the set point was increased to 43 pF/cm. Once the culture has also reached the 43 pF/cm the set point was again increased in 5 pF/cm steps until 85 pF/cm. The culture reached the 85 pF/cm after 18.6 dpi and was decreased again to 80 pF/cm. The culture was kept a that level for around 8 days followed by an further stepwise decrease of the set point to 70 pF/cm and 50 pF/cm. At the end of the fermentation the biomass was diluted to the permittivity that was reached directly after inoculation and the culture showed a normal grow like in classical batch fermentation. This experiment clearly demonstrates the robustness of the whole process against changes of the set point. This experiment clearly demonstrates that on the one hand the process is suited for a cultivation of a Pyrus communis cell culture and one the other hand that changes in the set point do not negatively influence the process.

6.) Time-Improvement

Figure 8:
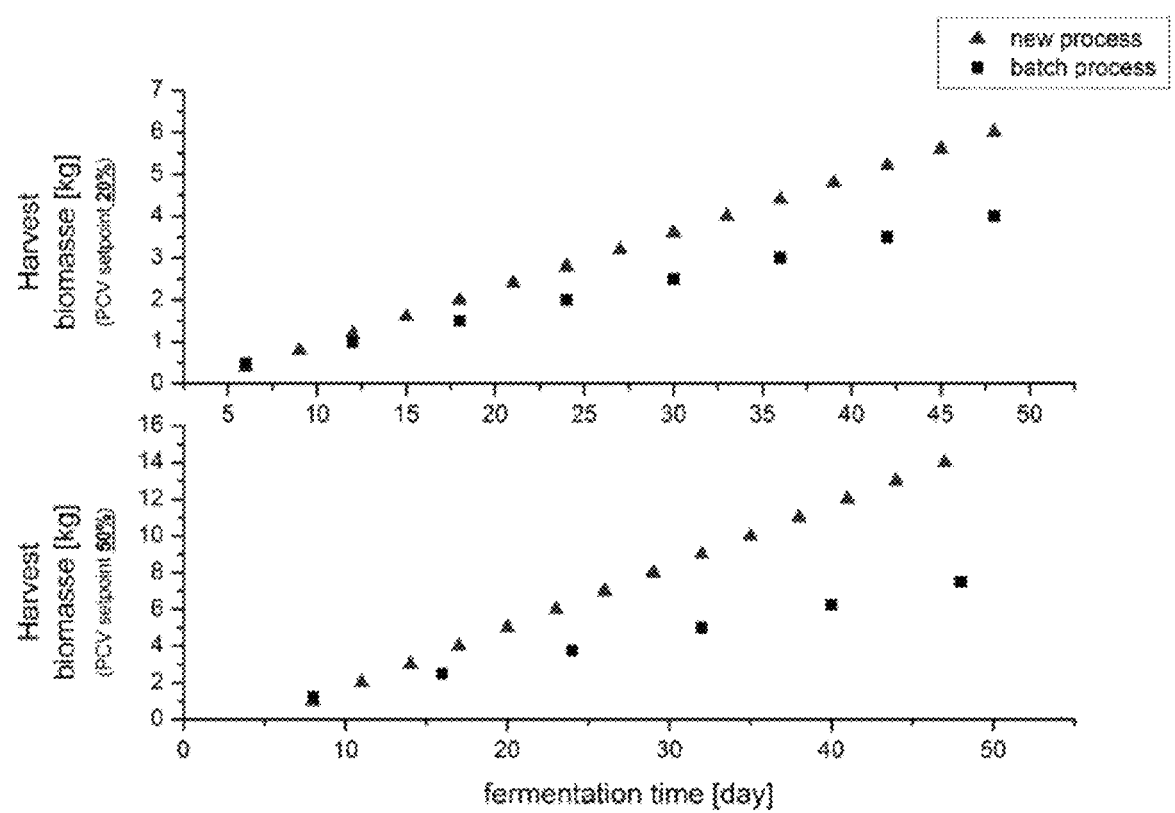
FIG. 8 is a diagram showing the improvements of using a process according to the present disclosure in comparison to a standard *N. tabacum* cv BY-2 batch fermentation depending on the permittivity set point.

The FIG. 8 shows a theoretical calculation of process times and harvested biomass based on the growth behavior of N. tabacum BY-2 cell cultures. The calculation for both fermentation strategies was based on a volume of 5 L cell suspension. The BY-2 cell culture needs 5 days to reach 20% PCV (100 mg/L fresh weight) in a batch culture and 7 days for a PCV of 50% (250 mg/L fresh weight) respectively. The setup time to clean, prepare and sterilize the vessel was the same for both fermentation strategies (1 day). For the classical batch fermentation the entire fermentation broth can be harvested (5 L) and for the new process the maximum harvest volume of 4 L was used to calculate. Once the new process is in the steady state every 3 days the maximal harvest volume could be removed from the vessel.

The upper part of the FIG. 8 shows the harvest of biomass over the time when the harvest criterion is 20% PCV (means in the new process the set point). The batch culture reached this biomass after 5 dpi. Both strategies provide the first harvest of biomass after 6 dpi. In the first batch the classical batch fermentation provides 0.5 kg of biomass and the new process 0.4 kg of Biomass. At that point the batch culture seems to be better. But once the harvest criteria (means in the new process the set point) is reached the new fermentation process needs only 3 day to again provide 0.4 kg of biomass instead of 6 days for 0.5 kg with a classical batch fermentation. If a time of 48 days is considered 8 classical batch fermentations can be conducted leading to a harvest of 4 kg biomass. In the same time frame 15 harvests that the new fermentation process can be conducted leading to 6 kg biomass. This is an increased Space-time Yield of about 50%. The increase in space-time-yield gets even higher if the harvest criteria are shifted to a PCV of 50% (250 mg/L) (FIG. 8 lower graph). The BY-2 cells need 8 days to reach that biomass. Considering 48 days 6 production cycles with the classical batch process can be conducted leading to 7.5 kg of biomass. With the new process 14 production cycles can be conducted in 47 days leading to a biomass of 14 kg and an increase of space-time-Yields of 86%. These data are combined in table 3.

TABLE 3

|  | Classical batch 20% PCV | New Process 20% PCV | Classical batch 50% PCV | New Process 50% PCV |
| --- | --- | --- | --- | --- |
| Harvest | 4 kg in 48 days | 6 kg in 48 days | 7.5 kg in 48 days | 14 kg in 47 days |
| Improvement |  | 50% better space-time-yields |  | 86% better Space-time-yields |

This graph shows the time improvements in comparison to a standard N. tabacum cv. BY-2 batch fermentation depending on the permittivity set point.

Figure 12:
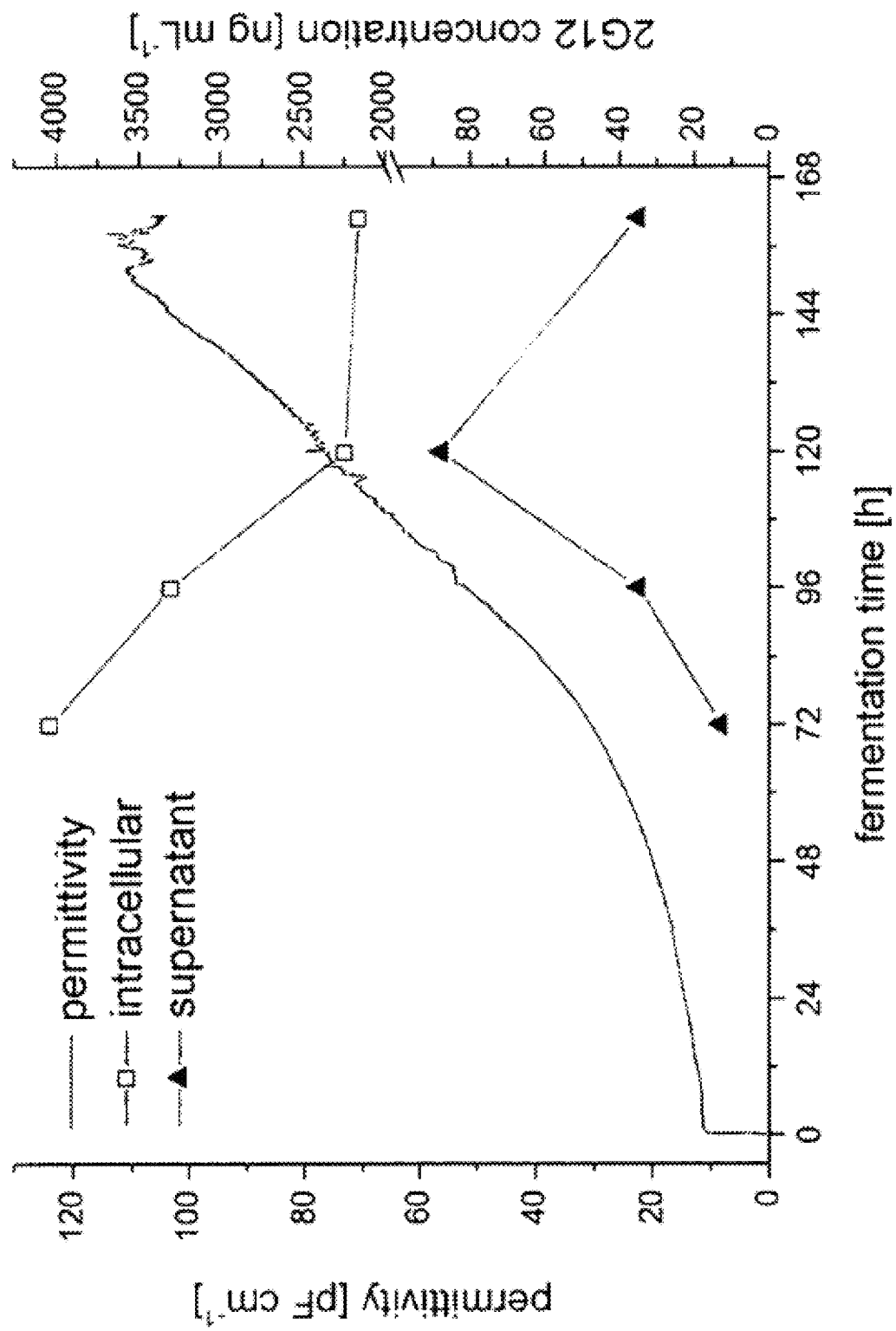
FIG. 12 is a diagram showing the permittivity of a transgenic *Nicotiana tabacum* BY-2 cell line and the 2G12 antibody concentration in the cells and the culture supernatant over the batch fermentation process.
Figure 13:
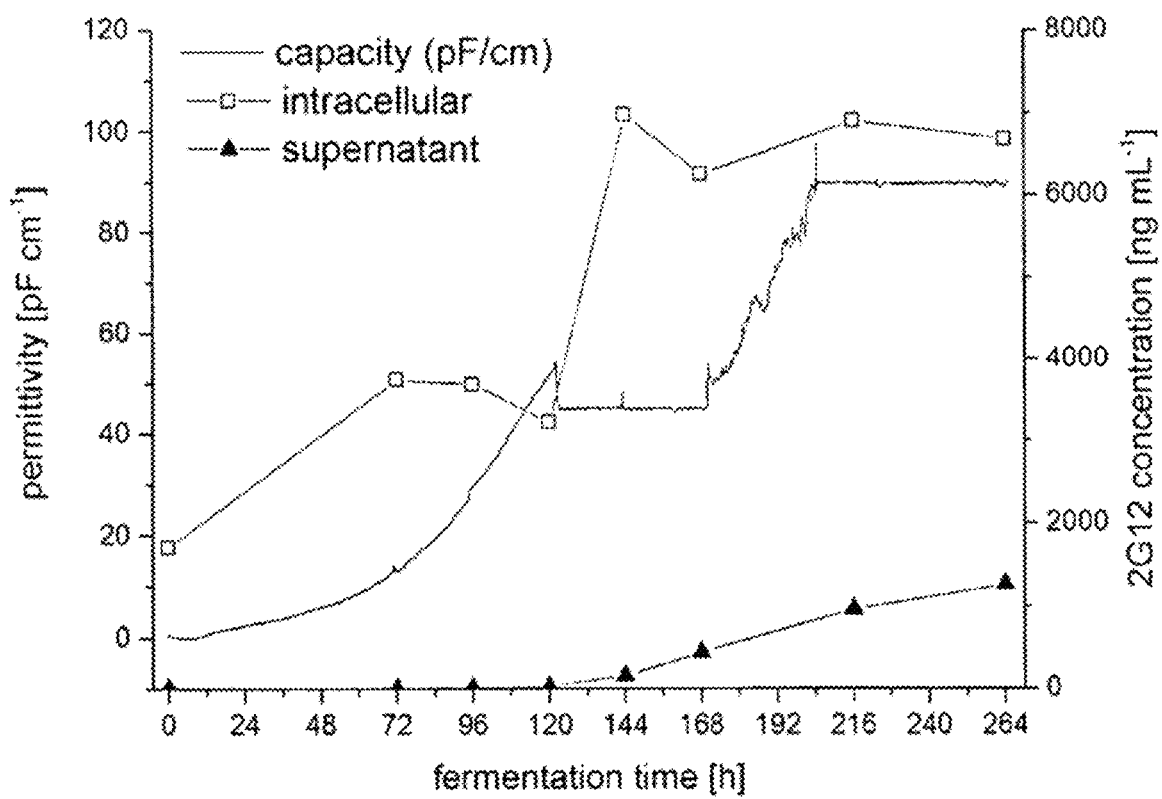
FIG. 13 is a diagram showing the permittivity of a transgenic *Nicotiana tabacum* BY-2 cell line and the 2G12 antibody concentration in the cells and the culture supernatant over the fermentation process according to the invention.

7.) Recombinant Antibody Production of a Transgenic BY-2 Cell Line in Batch Fermentation and With a Process According to the Present Disclosure A transgenic tobacco BY-2 cells suspension cell line (GFD#5) producing a HIV-1 neutralizing 2G12 antibody was generated by transformation with recombinant Agrobacteria carrying a binary T-DNA plasmid encoding the antibody heavy and light chain genes as described previously (Holland, Sack et al. 2010 Biotechnol Bioeng). The Batch fermentation and the analysis of 2G12 antibody accumulation by ELISA was performed as described previously (Holland, Sack et al. 2010 Biotechnol Bioeng). The batch fermentation was carried out for 161 hours. A 48 h lag phase was followed by the exponential cell growth phase of 104 h. The 2G12 concentration in the culture supernatant increased during exponential cell growth to a level of 88 ng/mL until 120 h of process time. Afterwards the concentration decreased in the next 41 h to a level of 35 ng/mL although the culture was still in the exponential growth phase. The intracellular concentration level was 4000 ng/mL after 72 h of process time and constantly decreased to a level of 2250 ng/mL after 120 h and stayed constant until the end of the process (FIG. 12). The fermentation according to the invention was performed as follows. The culture was inoculated with 5% (v/v) of a 7 days old pre culture. The starting volume was 1 L in a 3 L glass reactor. The minimal working volume of this reactor type is 0.5 L and the maximum working volume 2.7 L. After an initial batch Phase of 120 h the permittivity set point was set to 45 pF/cm and the controller loop has been started. Since the culture has already reached a permittivity of 54 pF/cm fresh medium was pumped into the reactor until a permittivity of 45 pF/cm was reached. This set point was then maintained constant for 48 h and afterwards increased to 90 pF/cm. The culture needed 37 h of growth to reach this permittivity level which was afterwards kept constant for another 58 h. In the initial phase (0-120 h fermentation time) both processes yielded comparable levels for the intracellular 2G12 concentration and the 2G12 concentration in the culture supernatant. In contrast to the batch fermentation the intracellular 2G12 concentration in the process according to this invention increased sharply to 7000 ng/mL after 120 h, and the higher product levels were maintained until the end of the fermentation process. The 2G12 antibody concentration in the culture supernatant also differed substantially to the batch fermentation process. In contrast to that the concentration did not decreases again but rather increased continuously over the entire process to a final product concentration of 1260 ng/mL (FIG. 13), a 14 fold increase compared to the maximum level of the batch fermentation.

The example clearly shows that the novel fermentation process according to the invention is not only suited for producing highly reproducible biomass, but also is useful for increasing the accumulation of recombinant proteins both in the cell culture supernatant and within the cells. In the batch fermentation the intracellular 2G12 antibody levels steadily decreased from 60 h till the harvest at 160 h from 4.0 µg/mL to 2.25 µg/mL. In contrast the 2G12 antibody levels in the novel process according to the invention increased from 3.7 µg/mL to 7.0 µg/mL from 120 h to 144 h, coinciding with the start of the phase where the permittivity is kept constant at 45 pF/cm. The intracellular 2G12 antibody levels increase did not only increase by almost a factor of two, but moreover it remained at the higher levels from 120 h-288 h. This also shows that the process according to the invention is characterized by less variability with respect to the intracellular product levels especially after the controller loop has been started after the initial growth phase.

The accumulation of the 2G12 antibody in the cell culture supernatant exhibited even higher differences. Whereas in the batch fermentation the levels peaked at 120 h and declined afterwards, a steady increase of the 2G12 antibody in the cell culture supernatant was observed for the novel fermentation process.

Surprisingly, the increase in 2G12 antibody levels were not only observed at medium cell densities corresponding to 45 pF/cm, but were also maintained (intracellular 2G12) or even further increased (cell culture supernatant 2G12) at 90 pF/cm. Thus, the 2G12 product levels in the cell culture supernatant also exhibited a lower variability, especially with longer process duration. The sustained increase of the 2G12 product levels in the cell culture supernatant furthermore demonstrate a higher robustness of the process according to the invention and its capacity to deliver a better product. This is evident from the fact that the 2G12 levels in the cell culture supernatant of the batch fermentation decreased again after 120 h, which means that the product has been degraded.

This example further shows that the set point for the permittivity can easily be changed within the process while not only maintaining cell growth and viability but also the accumulation of the recombinant protein product both within the cells and in the supernatant. This demonstrates the high robustness of the process according to the invention as well as its utility and unique options for process development and improvement.

7.) Fermentation of CHO Cells

A fermentation according to the invention was carried out with a transgenic CHO DG44 suspension cell line producing a monoclonal antibody and was performed as follows. The starting volume was 0.8 L of POWERCHO-2 CD®, without hypoxanthine and thymidine (Lonza, 12-771Q) supplemented with 4 mM L-Glutamine in a 3 L glass reactor (minimal working volume=0.5 L, maximal working volume=2.7) and the culture was inoculated with $2.8 \cdot 10^8$ cells. Dissolved oxygen concentration (dO2) was maintained at a 30% set point of saturation by automatically pulsing pressurized air into the fermenter using a sintered metal sparger at an aeration rate of 0.1 vvm (volume/volume/minute). Temperature was controlled at 37° C. and a fixed stirrer speed of 100 rpm was used. The pH was monitored and controlled at a set point of 7.0 with 0.5M NaOH. The fermentation was controlled using an EZCONTROL® (Applikon) and BIOXPERT XP® was used to collect the online data. Viable online biomass was measured using the FUTURA® RFIS system (Aber Instruments, Aberystwyth, UK). The permittivity of the cells and conductivity of the medium were measured simultaneously using an annular electrode (12×120 cm) and a standard remote FUTURA® instrument operating in cell culture mode at 0.6 MHz with polarization correction. The biomass sensor was controlled with FUTURA® software. In the cultivation process the actual process values were compared to the permittivity set-point in intervals of 5 s. A PID controller was used for process control. The specific setting of the P, I and D parameters were P-gain=20, I-time=0 and D-time=0. An Actuator transformed the controller output into an actuator output. When the permittivity signal exceeded the set-point a pump was controlled to add new sterile POWERCHO-2 CD® supplemented with 4 mM L-glutamine from a medium reservoir into the bioreactor, thus diluting the culture until the permittivity has reached the set-point.

After inoculation the fermentation a permittivity of 1.2 pF/cm was obtained corresponding to $3.5 \cdot 10^5$ cell/mL. The permittivity set point was defined as 3 pF/cm and the controller loop has been started. In the initial phase (batch phase) the cell density of the culture increased until this set point was reached. During this initial phase the cell culture volume did not change. Due to metabolic activity of the cell the dissolved oxygen concentration and the pH-value drops until their set point are reached.

Figure 14:
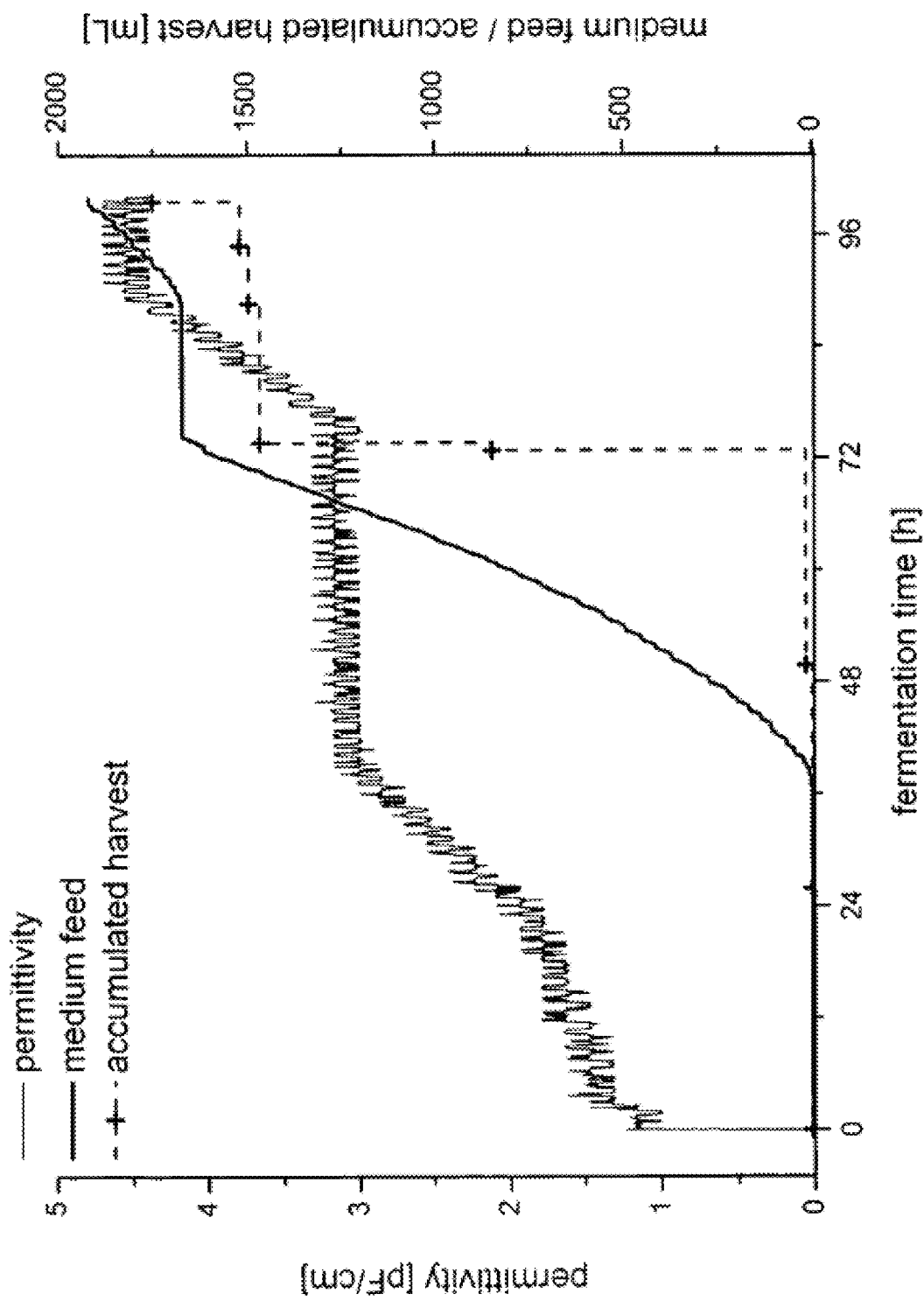
FIG. 14 is a diagram showing the permittivity, the medium feed volume and the accumulated harvest volume of a trangenic CHO DG44 cell culture over the entire process according to the invention.

After 26 h the cell density increased from $3.5 \cdot 10^5$ cell/mL to $6.8 \cdot 10^5$ cell/mL and the permittivity exhibited a corresponding change from 1.2 pF/cm to 2.3 pF/cm. The set point of 3 pF/cm was reached after 37 h of fermentation and was maintained thereafter. During this phase the culture volume increased (FIG. 14 medium feed). After 50 h an arbitrary volume of 10 mL was harvested without affecting the growing culture. At a fermentation time of 73.2 h another harvest of 830 mL was executed and 1 h later another 620 mL was harvested. Shortly thereafter (1.5 h) the set point was increased to 4.5 pF/cm and the new set point was reached after 14 h. During the second phase of constant permittivity of 4.5 pF/cm three more arbitrary cell culture fractions were harvested, without disturbing the cell culture.

The viability of the cells was determined by staining and counting in a THOMA® chamber or by CASY®. The results shown in table 4 demonstrate that the process according to the invention reproducibly delivers highly viable mammalian cells over the entire fermentation time. In particular high viable cells were also obtained at different permittivities. Furthermore the process also resulted in a high quality cell derived product, i.e. a monoclonal antibody. Of particular note the antibody product increased over the entire fermentation time. For comparison a fraction of the cell culture was harvested (hold step sample**) into a collection container after 73.2 h (*) of fermentation and a hold step was performed for 24 h on 4° C. The cell viability clearly decreased significantly from 94% to 85%. A comparison of the antibody concentration before (*) and after the hold step (**) also shows that the product concentration decreased from 40 µg/mL to 29 µg/mL (table 4). This clearly demonstrates the advantages of the process according to this invention.

TABLE 4

Permittivity, viable cell counts, viabilities and antibody concentration in the culture supernatant of the fermentation according to the invention with a transgenic CHO DG44 cell line

| Fermentation time [h] | Permittivity [pF/cm] | Cell count/ Cell viability CASY | Cell count/ Cell viability staining | Antibody concentration [µg/mL] |
| --- | --- | --- | --- | --- |
| 0 | 1.2 | $3.5 \cdot 10^5$/96% | n.d. | n.d. |
| 26 | 2.3 | $6.8 \cdot 10^5$/95% | n.d. | 14 |
| 50 | 3 | n.d. | $1.3 \cdot 10^5$/93% | 37 |
| 73.2(*) | 3 | n.d. | $1.3 \cdot 10^5$/94% | 40 |
| 89 | 4.5 | n.d | $1.9 \cdot 10^6$/94% | 51 |
| 95.3 | 4.5 | n.d. | $2.2 \cdot 10^6$/93% | 53 |
| Hold step sample** | 3 | n.d | $1.0 \cdot 10^6$/85% | 29 |

This example clearly shows that the process according to the invention is suitable also for mammalian cells to produce either highly reproducible viable cells or cell derived products, e.g. antibodies and recombinant proteins (FIG. 14).

REFERENCES

The contents of all cited references, including literature references, issued patents, and published patent applications, as cited throughout this application are hereby expressly incorporated by reference.

Baldi, L., D. Hacker, et al. (2012). Large-Scale Transfection of Mammalian Cells. *Protein Expression in Mammalian Cells.* J. L. Hartley, Humana Press. 801: 13-26.

Chmiel, H. (2006). Bioprozesstechnik, ELSEVIER, Spektrum akademischer Verlag.

Derouazi, M., P. Girard, et al. (2004). "Serum-free large-scale transient transfection of CHO cells." *Biotechnol Bioeng* 87(4): 537-545.

Douglas, K. L. (2008). "Toward development of artificial viruses for gene therapy: a comparative evaluation of viral and non-viral transfection." *Biotechnol Prog* 24(4): 871-883.

Geisse, S., M. Jordan, et al. (2005). "Large-scale transient expression of therapeutic proteins in mammalian cells." *Methods Mol Biol* 308: 87-98.

Gursinsky, T., B. Schulz, et al. (2009). "Replication of Tomato bushy stunt virus RNA in a plant in vitro system." *Virology* 390(2): 250-260.

Hacker, D. L., E. Derow, et al. (2005). "The CELO adenovirus Gam1 protein enhances transient and stable recombinant protein expression in Chinese hamster ovary cells." *J Biotechnol* 117(1): 21-29.

Holland T, Sack M, Rademacher T, Schmale K, Altmann F, Stadlmann J, Fischer R, Hellwig S. 2010. Optimal nitrogen supply as a key to increased and sustained production of a monoclonal full-size antibody in BY-2 suspension culture. Biotechnol Bioeng 107(2):278-89.

Jordan, M. and F. Wurm (2004). "Transfection of adherent and suspended cells by calcium phosphate." *Methods* 33(2): 136-143.

Komoda, K., S. Naito, et al. (2004). "Replication of plant RNA virus genomes in a cell-free extract of evacuolated plant protoplasts." *Proc Natl Acad Sci USA* 101(7): 1863-1867.

Pham, P., A. Kamen, et al. (2006). "Large-Scale transfection of mammalian cells for the fast production of recombinant protein." *Mol Biotechnol* 34(2): 225-237.

Sonobe, S. (1996). "Studies on the plant cytoskeleton using miniprotoplasts of tobacco BY-2 cells." *J. Plant Res.* 109(4): 437-448.

What is claimed is:

1. A cell-density regulated cell cultivation process for the production of eukaryotic cells and/or a eukaryotic cell-derived product, the process comprising the steps of:
   a) growing cells in a cell culture having a variable cell culture volume in a first cultivation vessel, wherein the culture volume is not regulated to be constant over the entire cell cultivation process,
   b) monitoring cell density in the cell culture over time by repeatedly performing cell density measurements with a density sensor,
   c) varying the cell culture volume to maintain the cells in growth phase by feeding nutrient medium into the cell culture in response to the monitored cell density,
   d) harvesting a fraction of the cell culture while maintaining remaining cells within the cell culture in growth phase, wherein feed rate and harvest rate are not coupled to one another, and wherein the harvested fraction comprises cells and/or a cell-derived product, and wherein the cell culture volume in the vessel is not kept constant continuously by adding nutrient medium into the vessel after harvesting said fraction and/or wherein the volume of the harvested fraction is not immediately replenished by adding nutrient medium into the vessel,
   e) repeating one or all of the aforementioned steps in the order set forth to allow a repeated harvest of cell culture fractions, and
   f) optionally processing the harvested cells and/or cell-derived products.

2. The process according to claim 1, wherein the cell density in the cell culture is measured continuously.

3. The process according to claim 1, wherein the cell density is regulated by using a control loop comprising a sensor continuously measuring the cell density which generates an and a controller generating an output signal that triggers a pump or valve or adding the appropriate volume of the nutrient medium to the cell culture.

4. The process according to claim 1, wherein the cell density in the cell culture is regulated to be constant over time or to be a specific time-dependent function for the cell density.

5. The process according to claim 1, wherein the first cultivation vessel is operated in a volume range between a minimal and a maximal cell culture filling level.

6. The process according to claim 1, wherein (i) at least one additional cultivation vessel is connected to the first cultivation vessel to increase the cultivation volume, (ii) the cell density in each connected cultivation vessel is maintained the same, and (iii) the cell culture is exchanged between the cultivation vessels.

7. The process according to claim 1, wherein the cells comprised in the harvested cell culture fraction are used to inoculate a subsequent fermentation process.

8. The process according to claim 1, wherein the harvested cells are used for performing a subsequent cultivation step, whereby (i) the cells are transfected/ transformed, (ii) gene expression is induced by the addition of an inducer, (iii) the cells are infected, (iv) the cells are cultivated under conditions that favor cell-derived product accumulation, (v) nucleic acids are transfected into the cells, and/or (vi) the cells are used for analytical assays.

9. The process according to claim 1, wherein the cells are used to prepare cell-free extracts.

10. A method for the preparation of cell free extract for an in vitro translation comprising the steps of:
   i) cultivating and harvesting cells according to the process of claim 1, and
   ii) obtaining a cell-free extract of the cultured cells by subjecting the harvested cells to an extraction treatment.

11. The method according to claim 10, wherein the harvested cells are in an exponentially growing phase.

12. The method according to claim 10, wherein extraction treatment comprises an enzymatic treatment.

13. A method for generating a stable cell line comprising the steps of:
   i) cultivating and harvesting cells according to the process of claim 1,
   ii) transforming the harvested cells with a nucleic acid to obtain a stable cell line.

14. A method for the generation of plant cell material in the form of a medium-deprived, porous structured and non-tissue multilayer cell pack and for the subsequent maintenance of said cell pack, comprising the steps of
   (i) cultivating and harvesting plant cells according to the process of claim 1 to produce a plant cell suspension;

(ii) separating the plant cell suspension of (i) to produce a cell pack having a porous structure, wherein the content of liquid comprised by the cell pack is reduced and adjusted to correspond to a cell pack density between 0.1 and 0.9 g wet cell weight per cm$^3$, thereby establishing the medium-deprived and porous structured nature of said cell pack, and (iii) incubating said medium-deprived and porous structured cell pack in a non-liquid environment under a relative humidity of 50 to 100%.

* * * * *